(12) United States Patent
Kallmeier et al.

(10) Patent No.: US 7,932,087 B2
(45) Date of Patent: Apr. 26, 2011

(54) METHOD OF EXPRESSING RECOMBINANT PROTEIN IN CHO CELLS

(75) Inventors: Robert Kallmeier, Holmer Green (GB); Robert Gay, Pinner Middx (GB)

(73) Assignee: Lonza Biologics PLC, Berkshire (GB)

( * ) Notice: Subject to any disclaimer, the term of this patent is extended or adjusted under 35 U.S.C. 154(b) by 230 days.

(21) Appl. No.: 11/962,261

(22) Filed: Dec. 21, 2007

(65) Prior Publication Data

US 2008/0138902 A1    Jun. 12, 2008

Related U.S. Application Data

(62) Division of application No. 10/521,768, filed as application No. PCT/EP03/07946 on Jul. 21, 2003, now abandoned.

(30) Foreign Application Priority Data

Jul. 19, 2002 (GB) ................................. 0216648.6

(51) Int. Cl.
   *C12N 15/85* (2006.01)
   *C07H 21/04* (2006.01)
(52) U.S. Cl. ...................................... 435/455; 536/24.1
(58) Field of Classification Search .................. None
   See application file for complete search history.

(56) References Cited

U.S. PATENT DOCUMENTS

| | | |
|---|---|---|
| 4,963,481 A | 10/1990 | deVilliers |
| 4,968,615 A | 11/1990 | Koszinowski et al. |
| 5,122,464 A | 6/1992 | Wilson et al. |
| 5,792,651 A | 8/1998 | Colpan et al. |
| 5,891,693 A | 4/1999 | Bebbington et al. |
| 6,743,622 B2 * | 6/2004 | Hollis et al. ............... 435/320.1 |

FOREIGN PATENT DOCUMENTS

| | | |
|---|---|---|
| WO | WO 95/11982 | 5/1995 |
| WO | 95 17516 A | 6/1995 |
| WO | WO 95/17516 | 6/1995 |
| WO | WO 2004/081167 | 9/2004 |

OTHER PUBLICATIONS

M. Cockett et al., "High Level Expression of Tissue Inhibitor of Metalloproteinases in Chinese Hamster Ovary Cells using Glutamine Synthetase Gene Amplification", Bio/Technology, Nature Publishing Co., New York, US, vol. 8, No. 7, Jul. 1990, pp. 662-667.
H. Pu et al., "Rapid Establishment of High-Producing Cell Lines Using Dicistronic Vectors with Glutamine Synthetase as the Selection Marker", Molecular Biotechnology, Totowa, NJ, US, vol. 10, 1998, pp. 17-25.
C. Bebbington et al., "High-Level Expression of a Recombinant Antibody from Myeloma Cells Using a Glutamine Synthetase Gene as an Amplifiable Selectable Marker", Bio/Technology, Nature Publishing Co., New York, US, vol. 10, No. 2, 1992, pp. 169-175.
J. Collins et al., "Germline Transcripts of the Murine Immunoglobulin Gamma-2a Gene: Structure and Induction by IFN-gamma", International Immunology, vol. 5, No. 8, 1993, pp. 885-891.
Bebbington et al (Biotechnology, 1992. vol. 10, pp. 169-175).
Dorsch-Hasler et al, "A long and complex enhancer activates transcription of the gene coding for the highly abundant immediate early mRNA in murine cytomegalovirus", Proc. Natl. Acad. Sci., vol. 82, pp. 8325-8329, Dec. 1985.
Rotondaro et al, "Efficiency of different viral promoters in directing gene expression in mammalian cells: effect of 3'-untranslated sequences", Gene, 168 (1996) 195-198.
Yu et al, "Characterization of Regulatory Elements Located Upstream of the Major Immediate Early Gene of Murine Cytomegalovirus", Korean Biochem. J. (1990), vol. 23, No. 2, pp. 160-165.
Priority document of EP 94718972 (European Application No. 03100617.4, filed Mar. 11, 2003).
Notice of Opposition to a European Patent dated Jul. 28, 2009, filed in EP 1 525 320.

* cited by examiner

*Primary Examiner* — Celine X Qian
(74) *Attorney, Agent, or Firm* — Nixon & Vanderhye P.C.

(57) ABSTRACT

Method of expressing recombinant protein in CHO cells, by using an expression vector comprising the murine IgG 2A gene locus.

5 Claims, 3 Drawing Sheets

SEQUENCE LISTING

<160> NUMBER OF SEQ ID NOS: 4

<210> SEQ ID NO 1
<211> LENGTH: 6679
<212> TYPE: DNA
<213> ORGANISM: Hamster sp.
<220> FEATURE:
<221> NAME/KEY: misc_feature
<223> OTHER INFORMATION: Seq. ID. No. 4: circular plasmid GS vector
      p12.4 short mCMV-GFP /clone 3

<400> SEQUENCE: 1
gaattcattg atcataatca gccataccac atttgtagag gttttacttg ctttaaaaaa      60
cctcccacac ctccccctga acctgaaaca taaaatgaat gcaattgttg ttgttaactt     120
gtttattgca gcttataatg gttacaaata aagcaatagc atcacaaatt tcacaaataa     180
agcatttttt tcactgcatt ctagttgtgg tttgtccaaa ctcatcaatg tatcttatca     240
tgtctggcgg ccgcgacctg caggcgcaga actggtaggt atggaagatc cctcgagatc     300
cattgtgctg gcggtaggcg agcagcgcct gcctgaagct gcgggcattc ccagtcagaa     360

```
atgagcgcca gtcgtcgtcg gctctcggca ccgaagtgct atgattctcc gccagcatgg    420
cttcggccag tgcgtcgagc agcgcccgct tgttcctgaa gtgccagtaa agcgccggct    480
gctgaacccc caaccgttcc gccagtttgc gtgtcgtcag accgtctacg ccgacctcgt    540
tcaacaggtc cagggcggca cggatcactg tattcggctg caactttgtc atgcttgaca    600
ctttatcact gataaacata atatgtccac caacttatca gtgataaaga atccgcgcca    660
gcacaatgga tctcgaggtc gagggatctc tagaggatcc atattcgcgg gcatcaccgg    720
cgccacaggt gcggttgctg gcgcctatat cgccgacatc accgatgggg aagatcgggc    780
tcgccacttc gggctcatga gcgcttgttt cggcgtgggt atggtggcag gccccgtggc    840
cgggggactg ttgggcgcca tctccttgca tgcaccattc cttgcggcgg cggtgctcaa    900
cggcctcaac ctactactgg gctgcttcct aatgcaggag tcgcataagg gagagcgtcg    960
acctcgggcc gcgttgctgg cgttttttcca taggctccgc ccccctgacg agcatcacaa   1020
aaatcgacgc tcaagtcaga ggtggcgaaa cccgacagga ctataaagat accaggcgtt   1080
tccccctgga agctccctcg tgcgctctcc tgttccgacc ctgccgctta ccggatacct   1140
gtccgccttt ctcccttcgg aagcgtggc gctttctcat agctcacgct gtaggtatct   1200
cagttcggtg taggtcgttc gctccaagct gggctgtgtg cacgaacccc ccgttcagcc   1260
cgaccgctgc gccttatccg gtaactatcg tcttgagtcc aacccggtaa gacacgactt   1320
atcgccactg gcagcagcca ctggtaacag gattagcaga gcgaggtatg taggcggtgc   1380
tacagagttc ttgaagtggt ggcctaacta cggctacact agaagaacag tatttggtat   1440
ctgcgctctg ctgaagccag ttaccttcgg aaaaagagtt ggtagctctt gatccggcaa   1500
acaaaccacc gctggtagcg gtggtttttt tgtttgcaag cagcagatta cgcgcagaaa   1560
aaaaggatct caagaagatc ctttgatctt ttctacgggg tctgacgctc agtggaacga   1620
aaactcacgt taagggattt tggtcatgag attatcaaaa aggatcttca cctagatcct   1680
tttaaattaa aaatgaagtt ttaaatcaat ctaaagtata tatgagtaaa cttggtctga   1740
cagttaccaa tgcttaatca gtgaggcacc tatctcagcg atctgtctat ttcgttcatc   1800
catagttgcc tgactccccg tcgtgtagat aactacgata cgggagggct taccatctgg   1860
ccccagtgct gcaatgatac cgcgagaccc acgctcaccg gctccagatt tatcagcaat   1920
aaaccagcca gccggaaggg ccgagcgcag aagtggtcct gcaactttat ccgcctccat   1980
ccagtctatt aattgttgcc gggaagctag agtaagtagt tcgccagtta atagtttgcg   2040
caacgttgtt gccattgcta caggcatcgt ggtgtcacgc tcgtcgtttg gtatggcttc   2100
attcagctcc ggttcccaac gatcaaggcg agttacatga tcccccatgt tgtgcaaaaa   2160
agcggttagc tccttcggtc ctccgatcgt tgtcagaagt aagttggccg cagtgttatc   2220
actcatggtt atgcagcac tgcataattc tcttactgtc atgccatccg taagatgctt   2280
ttctgtgact ggtgagtact caaccaagtc attctgagaa tagtgtatgc ggcgaccgag   2340
ttgctcttgc ccggcgtcaa tacgggataa taccgcgcca catagcagaa ctttaaaagt   2400
gctcatcatt ggaaaacgtt cttcggggcg aaaactctca aggatcttac cgctgttgag   2460
atccagttcg atgtaaccca ctcgtgcacc caactgatct tcagcatctt ttactttcac   2520
cagcgtttct gggtgagcaa aaacaggaag gcaaaatgcc gcaaaaaagg gaataagggc   2580
gacacggaaa tgttgaatac tcatactctt cctttttcaa tattattgaa gcatttatca   2640
gggttattgt ctcatgagcg gatacatatt tgaatgtatt tagaaaaata aacaaatagg   2700
ggttccgcgc acatttcccc gaaaagtgcc acctgacgtc taagaaacca ttattatcat   2760
```

-continued

| | |
|---|---|
| gacattaacc tataaaaata ggcgtatcac gaggccctga tggctctttg cggcacccat | 2820 |
| cgttcgtaat gttccgtggc accgaggaca accctcaaga gaaaatgtaa tcacactggc | 2880 |
| tcaccttcgg gtgggccttt ctgcgtttat aaggagacac tttatgttta agaaggttgg | 2940 |
| taaattcctt gcggctttgg cagccaagct agatccggct gtggaatgtg tgtcagttag | 3000 |
| ggtgtggaaa gtccccaggc tccccagcag gcagaagtat gcaaagcatg catctcaatt | 3060 |
| agtcagcaac caggtgtgga aagtcccccag gctcccccagc aggcagaagt atgcaaagca | 3120 |
| tgcatctcaa ttagtcagca accatagtcc cgcccctaac tccgcccatc ccgcccctaa | 3180 |
| ctccgcccag ttccgcccat tctccgcccc atggctgact aattttttttt atttatgcag | 3240 |
| aggccgaggc cgcctcggcc tctgagctat ccagaagta gtgaggaggc ttttttggag | 3300 |
| gcctaggctt ttgcaaaaag ctagcttggg gccaccgctc agagcacctt ccaccatggc | 3360 |
| cacctcagca agttcccact tgaacaaaaa catcaagcaa atgtacttgt gcctgcccca | 3420 |
| gggtgagaaa gtccaagcca tgtatatctg ggttgatggt actggagaag gactgcgctg | 3480 |
| caaaacccgc accctggact gtgagcccaa gtgtgtagaa gagttacctg agtggaattt | 3540 |
| tgatggctct agtaccttttc agtctgaggg ctccaacagt gacatgtatc tcagccctgt | 3600 |
| tgccatgttt cgggacccct tccgcagaga tcccaacaag ctggtgttct gtgaagtttt | 3660 |
| caagtacaac cggaagcctg cagagaccaa tttaaggcac tcgtgtaaac ggataatgga | 3720 |
| catggtgagc aaccagcacc cctggtttgg aatggaacag gagtatactc tgatgggaac | 3780 |
| agatgggcac ccttttggtt ggccttccaa tggctttcct gggccccaag gtccgtatta | 3840 |
| ctgtggtgtg ggcgcagaca aagcctatgg cagggatatc gtggaggctc actaccgcgc | 3900 |
| ctgcttgtat gctggggtca agattacagg aacaaatgct gaggtcatgc ctgcccagtg | 3960 |
| ggaactccaa ataggaccct gtgaaggaat ccgcatggga gatcatctct gggtggcccg | 4020 |
| tttcatcttg catcgagtat gtgaagactt tgggtaata gcaacctttg accccaagcc | 4080 |
| cattcctggg aactggaatg gtgcaggctg ccataccaac tttagcacca aggccatgcg | 4140 |
| ggaggagaat ggtctgaagc acatcgagga ggccatcgag aaactaagca agcggcaccg | 4200 |
| gtaccacatt cgagcctacg atcccaaggg gggcctggac aatgcccgtg gtctgactgg | 4260 |
| gttccacgaa acgtccaaca tcaacgactt ttctgctggt gtcgccaatc gcagtgccag | 4320 |
| catccgcatt ccccggactg tcggccagga gaagaaaggt tactttgaag accgcggccc | 4380 |
| ctctgccaat tgtgaccccc ttgcagtgac agaagccatc gtccgcacat gccttctcaa | 4440 |
| tgagactggc gacgagccct tccaatacaa aaactaatta gactttgagt gatcttgagc | 4500 |
| ctttcctagt tcatcccacc ccgccccaga gagatctttg tgaaggaacc ttacttctgt | 4560 |
| ggtgtgacat aattggacaa actacctaca gagatttaaa gctctaaggt aaatataaaa | 4620 |
| tttttaagtg tataatgtgt taaactactg attctaattg tttgtgtatt ttagattcca | 4680 |
| acctatggaa ctgatgaatg ggagcagtgg tggaatgcct ttaatgagga aaacctgttt | 4740 |
| tgctcagaag aaatgccatc tagtgatgat gaggctactg ctgactctca acattctact | 4800 |
| cctccaaaaa agaagagaaa ggtagaagac cccaaggact tccttcaga attgctaagt | 4860 |
| tttttgagtc atgctgtgtt tagtaataga actcttgctt gctttgctat ttacaccaca | 4920 |
| aaggaaaaag ctgcactgct atacaagaaa attatgaaa atattctgt aacctttata | 4980 |
| agtaggcata acagttataa tcataacata ctgttttttc ttactccaca caggcataga | 5040 |
| gtgtctgcta ttaataacta tgctcaaaaa ttgtgtacct ttagcttttt aatttgtaaa | 5100 |
| ggggttaata aggaatattt gatgtatagt gccttgacta gagatcataa tcagccatac | 5160 |

-continued

```
cacatttgta gaggttttac ttgctttaaa aaacctccca cacctccccc tgaacctgaa      5220
acataaaatg aatgcaattg ttgttgttaa cttgtttatt gcagcttata atggttacaa      5280
ataaagcaat agcatcacaa atttcacaaa taaagcattt ttttcactgc attctagttg      5340
tggtttgtcc aaactcatca atgtatctta tcatgtctgg atctctagct tcgtgtcaag      5400
gacggtgagg cgcgcctact gagtcattag ggactttcca atgggttttg cccagtacat      5460
aaggtcaata ggggtgaatc aacaggaaag tcccattgga gccaagtaca ctgagtcaat      5520
agggactttc cattgggttt tgcccagtac aaaaggtcaa taggggtga gtcaatgggt       5580 ttttcccatt attggcacgt acataaggtc aataggggtg agtcattggg ttttccagc       5640 caatttaatt aaaacgccat gtactttccc accattgacg tcaatgggct attgaaacta      5700
atgcaacgtg acctttaaac ggtactttcc catagctgat taatgggaaa gtaccgttct      5760
cgagccaata cacgtcaatg ggaagtgaaa gggcagccaa acgtaacac cgccccggtt       5820 ttcccctgga aattccatat tggcacgcat tctattggct gagctgcgtt ctacgtgggt      5880
ataagaggcg cgaccagcgt cggtaccgtc gcagtcttcg gtctgaccac cgtagaacgc      5940
agaagcttgc cgccaccatg gtgagcaagc agatcctgaa gaacaccggc ctgcaggaga      6000
tcatgagctt caaggtgaac ctggagggcg tggtgaacaa ccacgtgttc accatggagg      6060
gctgcggcaa gggcaacatc ctgttcggca accagctggt gcagatccgc gtgaccaagg      6120 gcgccccct gcccttcgcc ttcgacatcc tgagccccgc cttccagtac ggcaaccgca      6180
ccttcaccaa gtaccccgag gacatcagcg acttcttcat ccagagcttc cccgccggct      6240
tcgtgtacga gcgcacctg cgctacgagg acggcggcct ggtggagatc gcagcgaca       6300 tcaacctgat cgaggagatg ttcgtgtacc gcgtggagta caagggccgc aacttccca       6360 acgacggccc cgtgatgaag aagaccatca ccggcctgca gcccagcttc gaggtggtgt      6420
acatgaacga cggcgtgctg gtgggccagg tgatcctggt gtaccgcctg aacagcggca      6480
agttctacag ctgccacatg cgcacccga tgaagagcaa gggcgtggtg aaggacttcc       6540
ccgagtacca cttcatccag caccgcctgg agaagaccta cgtggaggac ggcggcttcg      6600
tggagcagca cgagaccgcc atcgcccagc tgaccagcct gggcaagccc ctgggcagcc      6660
tgcacgagtg ggtgtaata                                                    6679
```

<210> SEQ ID NO 2
<211> LENGTH: 8251
<212> TYPE: DNA
<213> ORGANISM: Hamster sp.
<220> FEATURE:
<221> NAME/KEY: misc_feature
<223> OTHER INFORMATION: Seq. ID. No. 3: circular plasmid GS vector
    p12.4 hCMVp-GFP /clone 13

<400> SEQUENCE: 2

```
gaattcattg atcataatca gccataccac atttgtagag gttttacttg ctttaaaaaa        60
cctcccacac ctcccctga acctgaaaca taaaatgaat gcaattgttg ttgttaactt       120
gtttattgca gcttataatg gttacaaata aagcaatagc atcacaaatt tcacaaataa       180 agcattttt tcactgcatt ctagttgtgg tttgtccaaa ctcatcaatg tatcttatca       240
tgtctggcgg ccgcgacctg caggcgcaga actggtaggt atggaagatc cctcgagatc       300
cattgtgctg gcggtaggcg agcagcgcct gcctgaagct gcgggcattc ccagtcagaa       360
atgagcgcca gtcgtcgtcg gctctcggca ccgaagtgct atgattctcc gccagcatgg       420
cttcggccag tgcgtcgagc agcgcccgct tgttcctgaa gtgccagtaa agcgccggct       480
```

```
gctgaacccc caaccgttcc gccagtttgc gtgtcgtcag accgtctacg ccgacctcgt    540
tcaacaggtc cagggcggca cggatcactg tattcggctg caactttgtc atgcttgaca    600
ctttatcact gataaacata atatgtccac caacttatca gtgataaaga atccgcgcca    660
gcacaatgga tctcgaggtc gagggatctc tagaggatcc atattcgcgg gcatcaccgg    720
cgccacaggt gcggttgctg gcgcctatat cgccgacatc accgatgggg aagatcgggc    780
tcgccacttc gggctcatga gcgcttgttt cggcgtgggt atggtggcag gccccgtggc    840
cgggggactg ttgggcgcca tctccttgca tgcaccattc cttgcggcgg cggtgctcaa    900
cggcctcaac ctactactgg gctgcttcct aatgcaggag tcgcataagg gagagcgtcg    960
acctcgggcc gcgttgctgg cgttttttcca taggctccgc ccccctgacg agcatcacaa   1020
aaatcgacgc tcaagtcaga ggtggcgaaa cccgacagga ctataaagat accaggcgtt   1080
tcccctgga agctccctcg tgcgctctcc tgttccgacc ctgccgctta ccggatacct    1140
gtccgccttt ctcccttcgg gaagcgtggc gctttctcat agctcacgct gtaggtatct   1200
cagttcggtg taggtcgttc gctccaagct gggctgtgtg cacgaacccc ccgttcagcc   1260
cgaccgctgc gccttatccg gtaactatcg tcttgagtcc aacccggtaa gacacgactt   1320
atcgccactg gcagcagcca ctggtaacag gattagcaga gcgaggtatg taggcggtgc   1380
tacagagttc ttgaagtggt ggcctaacta cggctacact agaagaacag tatttggtat   1440
ctgcgctctg ctgaagccag ttaccttcgg aaaaagagtt ggtagctctt gatccggcaa   1500
acaaaccacc gctggtagcg gtggtttttt tgtttgcaag cagcagatta cgcgcagaaa   1560
aaaaggatct caagaagatc ctttgatctt ttctacgggg tctgacgctc agtggaacga   1620
aaactcacgt taagggattt tggtcatgag attatcaaaa aggatcttca cctagatcct   1680
tttaaattaa aaatgaagtt ttaaatcaat ctaaagtata tatgagtaaa cttggtctga   1740
cagttaccaa tgcttaatca gtgaggcacc tatctcagcg atctgtctat ttcgttcatc   1800
catagttgcc tgactccccg tcgtgtagat aactacgata cgggagggct taccatctgg   1860
ccccagtgct gcaatgatac cgcgagaccc acgctcaccg gctccagatt tatcagcaat   1920
aaaccagcca gccggaaggg ccgagcgcag aagtggtcct gcaactttat ccgcctccat   1980
ccagtctatt aattgttgcc gggaagctag agtaagtagt tcgccagtta atagtttgcg   2040
caacgttgtt gccattgcta caggcatcgt ggtgtcacgc tcgtcgtttg gtatggcttc   2100
attcagctcc ggttcccaac gatcaaggcg agttacatga tcccccatgt tgtgcaaaaa   2160
agcggttagc tccttcggtc ctccgatcgt tgtcagaagt aagttggccg cagtgttatc   2220
actcatggtt atggcagcac tgcataattc tcttactgtc atgccatccg taagatgctt   2280
ttctgtgact ggtgagtact caaccaagtc attctgagaa tagtgtatgc ggcgaccgag   2340
ttgctcttgc ccggcgtcaa tacgggataa taccgcgcca catagcagaa ctttaaaagt   2400
gctcatcatt ggaaaacgtt cttcggggcg aaaactctca aggatcttac cgctgttgag   2460
atccagttcg atgtaaccca ctcgtgcacc caactgatct tcagcatctt ttactttcac   2520
cagcgtttct gggtgagcaa aaacaggaag gcaaaatgcc gcaaaaaagg gaataagggc   2580
gacacggaaa tgttgaatac tcatactctt ccttttcaa tattattgaa gcatttatca   2640
gggttattgt ctcatgagcg gatacatatt tgaatgtatt tagaaaaata acaaataggg   2700
ggttccgcgc acatttcccc gaaaagtgcc acctgacgtc taagaaacca ttattatcat   2760
gacattaacc tataaaaata ggcgtatcac gaggcccctga tggctctttg cggcacccat   2820
cgttcgtaat gttccgtggc accgaggaca accctcaaga gaaaatgtaa tcacactggc   2880
```

```
tcaccttcgg gtgggccttt ctgcgtttat aaggagacac tttatgttta agaaggttgg    2940
taaattcctt gcggctttgg cagccaagct agatccggct gtggaatgtg tgtcagttag    3000
ggtgtggaaa gtccccaggc tccccagcag gcagaagtat gcaaagcatg catctcaatt    3060
agtcagcaac caggtgtgga aagtcccag gctcccagc aggcagaagt atgcaaagca    3120
tgcatctcaa ttagtcagca accatagtcc cgccctaac tccgcccatc ccgcccctaa    3180
ctccgcccag ttccgcccat tctccgcccc atggctgact aatttttttt atttatgcag    3240
aggccgaggc cgcctcggcc tctgagctat ccagaagta gtgaggaggc ttttttggag    3300
gcctaggctt ttgcaaaaag ctagcttggg gccaccgctc agagcacctt ccaccatggc    3360
cacctcagca agttcccact tgaacaaaaa catcaagcaa atgtacttgt gcctgcccca    3420
gggtgagaaa gtccaagcca tgtatatctg ggttgatggt actggagaag gactgcgctg    3480
caaaacccgc accctggact gtgagcccaa gtgtgtagaa gagttacctg agtggaattt    3540
tgatggctct agtaccttc agtctgaggg ctccaacagt gacatgtatc tcagccctgt    3600
tgccatgttt cgggacccct tccgcagaga tcccaacaag ctggtgttct gtgaagtttt    3660
caagtacaac cggaagcctg cagagaccaa tttaaggcac tcgtgtaaac ggataatgga    3720
catggtgagc aaccagcacc cctggttgg aatggaacag gagtatactc tgatgggaac    3780
agatgggcac ccttttggtt ggccttccaa tggctttcct gggccccaag gtccgtatta    3840
ctgtggtgtg ggcgcagaca aagcctatgg cagggatatc gtggaggctc actaccgcgc    3900
ctgcttgtat gctggggtca agattacagg aacaaatgct gaggtcatgc ctgcccagtg    3960
ggaactccaa ataggaccct gtgaaggaat ccgcatggga gatcatctct gggtggcccg    4020
tttcatcttg catcgagtat gtgaagactt tggggtaata gcaaccttg accccaagcc    4080 cattcctggg aactggaatg gtgcaggctg ccataccaac tttagcacca aggccatgcg    4140
ggaggagaat ggtctgaagc acatcgagga ggccatcgag aaactaagca agcggcaccg    4200
gtaccacatt cgagcctacg atcccaaggg gggcctggac aatgcccgtg gtctgactgg    4260
gttccacgaa acgtccaaca tcaacgactt ttctgctggt gtcgccaatc gcagtgccag    4320
catccgcatt ccccggactg tcggccagga gaagaaaggt tactttgaag accgcggccc    4380
ctctgccaat tgtgacccct ttgcagtgac agaagccatc gtccgcacat gccttctcaa    4440
tgagactggc gacgagccct tccaatacaa aaactaatta gactttgagt gatcttgagc    4500
ctttcctagt tcatcccacc ccgccccaga gagatctttg tgaaggaacc ttacttctgt    4560
ggtgtgacat aattggacaa actacctaca gagatttaaa gctctaaggt aaatataaaa    4620
tttttaagtg tataatgtgt taaactactg attctaattg tttgtgtatt ttagattcca    4680
acctatggaa ctgatgaatg ggagcagtgg tggaatgcct ttaatgagga aaacctgttt    4740
tgctcagaag aaatgccatc tagtgatgat gaggctactg ctgactctca acattctact    4800
cctccaaaaa agaagagaaa ggtagaagac cccaaggact tccttcaga attgctaagt    4860 ttttgagtc atgctgtgtt tagtaataga actcttgctt gctttgctat ttacaccaca    4920
aaggaaaaag ctgcactgct atacaagaaa attatgaaa aatattctgt aacctttata    4980
agtaggcata acagttataa tcataacata ctgtttttc ttactccaca caggcataga    5040
gtgtctgcta ttaataacta tgctcaaaaa ttgtgtacct ttagcttttt aatttgtaaa    5100
ggggttaata aggaatattt gatgtatagt gccttgacta gagatcataa tcagccatac    5160
cacatttgta gaggttttac ttgctttaaa aaacctccca cacctccccc tgaacctgaa    5220
acataaaatg aatgcaattg ttgttgttaa cttgtttatt gcagcttata atggttacaa    5280
```

```
ataaagcaat agcatcacaa atttcacaaa taaagcattt ttttcactgc attctagttg    5340
tggtttgtcc aaactcatca atgtatctta tcatgtctgg atctagcttc gtgtcaagga    5400
cggtgactgc agtgaataat aaaatgtgtg tttgtccgaa atacgcgttt tgagatttct    5460
gtcgccgact aaattcatgt cgcgcgatag tggtgtttat cgccgataga gatggcgata    5520
ttggaaaaat cgatatttga aaatatggca tattgaaaat gtcgccgatg tgagtttctg    5580
tgtaactgat atcgccattt ttccaaaagt gattttthggg catacgcgat atctggcgat    5640
agcgcttata tcgtttacgg gggatggcga tagacgactt tggtgacttg ggcgattctg    5700
tgtgtcgcaa atatcgcagt ttcgatatag gtgacagacg atatgaggct atatcgccga    5760
tagaggcgac atcaagctgg cacatggcca atgcatatcg atctatacat tgaatcaata    5820
ttggccatta gccatattat tcattggtta tatagcataa atcaatattg gctattggcc    5880
attgcatacg ttgtatccat atcataatat gtacatttat attggctcat gtccaacatt    5940
accgccatgt tgacattgat tattgactag ttattaatag taatcaatta cggggtcatt    6000
agttcatagc ccatatatgg agttccgcgt tacataactt acggtaaatg gcccgcctgg    6060
ctgaccgccc aacgaccccc gcccattgac gtcaataatg acgtatgttc ccatagtaac    6120
gccaataggg actttccatt gacgtcaatg ggtggagtat ttacggtaaa ctgcccactt    6180
ggcagtacat caagtgtatc atatgccaag tacgccccct attgacgtca atgacggtaa    6240
atggcccgcc tggcattatg cccagtacat gaccttatgg gactttccta cttggcagta    6300
catctacgta ttagtcatcg ctattaccat ggtgatgcgg ttttggcagt acatcaatgg    6360
gcgtggatag cggtttgact cacggggatt tccaagtctc cacccccattg acgtcaatgg    6420 gagtttgttt tggcaccaaa atcaacggga ctttccaaaa tgtcgtaaca actccgcccc    6480
attgacgcaa atgggcggta ggcgtgtacg gtgggaggtc tatataagca gagctcgttt    6540
agtgaaccgt cagatcgcct ggagacgcca tccacgctgt tttgacctcc atagaagaca    6600
ccgggaccga tccagcctcc gcggccggga acggtgcatt ggaacgcgga ttccccgtgc    6660
caagagtgac gtaagtaccg cctatagagt ctataggccc accccccttgg cttcttatgc    6720 atgctatact gttttttggct tggggtctat acaccccccgc ttcctcatgt tataggtgat    6780
ggtatagctt agcctatagg tgtgggttat tgaccattat tgaccactcc cctattggtg    6840
acgatacttt ccattactaa tccataacat ggctctttgc cacaactctc tttattggct    6900
atatgccaat acactgtcct tcagagactg acacggactc tgtattttta caggatgggg    6960 tctcattttat tatttacaaa ttcacatata caacaccacc gtccccagtg cccgcagttt    7020
ttattaaaca taacgtggga tctccacgcg aatctcgggt acgtgttccg gacatgggct    7080
cttctccggt agcggcggag cttctacatc cgagccctgc tcccatgcct ccagcgactc    7140
atggtcgctc ggcagctcct tgctcctaac agtggaggcc agacttaggc acagcacgat    7200
gcccaccacc accagtgtgc cgcacaaggc cgtggcggta gggtatgtgt ctgaaaatga    7260
gctcggggag cgggcttgca ccgctgacgc atttggaaga cttaaggcag cggcagaaga    7320
agatgcaggc agctgagttg ttgtgttctg ataagagtca gaggtaactc ccgttgcggt    7380
gctgttaacg gtggagggca gtgtagtctg agcagtactc gttgctgccg cgcgcgccac    7440
cagacataat agctgacaga ctaacagact gttcctttcc atgggtcttt tctgcagtca    7500
ccgtccttga cacgaagctt gccgccacca tggtgagcaa gcagatcctg aagaacaccg    7560
gcctgcagga gatcatgagc ttcaaggtga acctggaggg cgtggtgaac aaccacgtgt    7620
tcaccatgga gggctgcggc aagggcaaca tcctgttcgg caaccagctg gtgcagatcc    7680
```

| | |
|---|---|
| gcgtgaccaa gggcgccccc ctgcccttcg ccttcgacat cctgagcccc gccttccagt | 7740 |
| acggcaaccg caccttcacc aagtaccccg aggacatcag cgacttcttc atccagagct | 7800 |
| tccccgccgg cttcgtgtac gagcgcaccc tgcgctacga ggacggcggc ctggtggaga | 7860 |
| tccgcagcga catcaacctg atcgaggaga tgttcgtgta ccgcgtggag tacaagggcc | 7920 |
| gcaacttccc caacgacggc cccgtgatga agaagaccat caccggcctg cagcccagct | 7980 |
| tcgaggtggt gtacatgaac gacggcgtgc tggtgggcca ggtgatcctg gtgtaccgcc | 8040 |
| tgaacagcgg caagttctac agctgccaca tgcgcaccct gatgaagagc aagggcgtgg | 8100 |
| tgaaggactt ccccgagtac cacttcatcc agcaccgcct ggagaagacc tacgtggagg | 8160 |
| acggcggctt cgtggagcag cacgagaccg ccatcgccca gctgaccagc ctgggcaagc | 8220 |
| ccctgggcag cctgcacgag tgggtgtaat a | 8251 |

<210> SEQ ID NO 3
<211> LENGTH: 10369
<212> TYPE: DNA
<213> ORGANISM: Hamster sp.
<220> FEATURE:
<221> NAME/KEY: misc_feature
<223> OTHER INFORMATION: Seq. ID. No. 2: circular plasmid GS-minigene
    vector p 14.4 DeltaM odulator (mod-) hCMVp-GFP /clone 6

<400> SEQUENCE: 3

| | |
|---|---|
| gaattcattg atcataatca gccataccac atttgtagag gttttacttg ctttaaaaaa | 60 |
| cctcccacac ctccccctga acctgaaaca taaaatgaat gcaattgttg ttgttaactt | 120 |
| gtttattgca gcttataatg gttacaaata aagcaatagc atcacaaatt tcacaaataa | 180 |
| agcattttt tcactgcatt ctagttgtgg tttgtccaaa ctcatcaatg tatcttatca | 240 |
| tgtctggcgg ccgcgacctg caggcgcaga actggtaggt atggaagatc cctcgagatc | 300 |
| cattgtgctg gcgtaggcg agcagcgcct gcctgaagct gcgggcattc ccagtcagaa | 360 |
| atgagcgcca gtcgtcgtcg gctctcggca ccgaagtgct atgattctcc gccagcatgg | 420 |
| cttcggccag tgcgtcgagc agcgcccgct tgttcctgaa gtgccagtaa agcgccggct | 480 |
| gctgaacccc caaccgttcc gccagtttgc gtgtcgtcag accgtctacg ccgacctcgt | 540 |
| tcaacaggtc cagggcggca cggatcactg tattcggctg caactttgtc atgcttgaca | 600 |
| ctttatcact gataaacata atatgtccac caacttatca gtgataaaga atccgcgcca | 660 |
| gcacaatgga tctcgaggtc gagggatctc tagaggatcc atattcgcgg gcatcaccgg | 720 |
| cgccacaggt gcggttgctg gcgcctatat cgccgacatc accgatgggg aagatcgggc | 780 |
| tcgccacttc gggctcatga gcgcttgttt cggcgtgggt atggtggcag gccccgtggc | 840 |
| cggggggactg ttgggcgcca tctccttgca tgcaccattc cttgcggcgg cggtgctcaa | 900 |
| cggcctcaac ctactactgg gctgcttcct aatgcaggag tcgcataagg gagagcgtcg | 960 |
| acctcgggcc gcgttgctgg cgttttttcca taggctccgc cccctgacg agcatcacaa | 1020 |
| aaatcgacgc tcaagtcaga ggtggcgaaa cccgacagga ctataaagat accaggcgtt | 1080 |
| tccccctgga agctccctcg tgcgctctcc tgttccgacc ctgccgctta ccggatacct | 1140 |
| gtccgccttt ctcccttcgg gaagcgtggc gctttctcat agctcacgct gtaggtatct | 1200 |
| cagttcggtg taggtcgttc gctccaagct gggctgtgtg cacgaacccc ccgttcagcc | 1260 |
| cgaccgctgc gccttatccg gtaactatcg tcttgagtcc aacccggtaa gacacgactt | 1320 |
| atcgccactg gcagcagcca ctggtaacag gattagcaga gcgaggtatg taggcggtgc | 1380 |
| tacagagttc ttgaagtggt ggcctaacta cggctacact agaagaacag tatttggtat | 1440 |

```
ctgcgctctg ctgaagccag ttaccttcgg aaaaagagtt ggtagctctt gatccggcaa    1500
acaaaccacc gctggtagcg gtggttttttt tgtttgcaag cagcagatta cgcgcagaaa    1560
aaaaggatct caagaagatc ctttgatctt ttctacgggg tctgacgctc agtggaacga    1620
aaactcacgt taagggattt tggtcatgag attatcaaaa aggatcttca cctagatcct    1680
tttaaattaa aaatgaagtt ttaaatcaat ctaaagtata tatgagtaaa cttggtctga    1740
cagttaccaa tgcttaatca gtgaggcacc tatctcagcg atctgtctat ttcgttcatc    1800
catagttgcc tgactccccg tcgtgtagat aactacgata cgggagggct taccatctgg    1860
ccccagtgct gcaatgatac cgcgagaccc acgctcaccg gctccagatt tatcagcaat    1920
aaaccagcca gccggaaggg ccgagcgcag aagtggtcct gcaactttat ccgcctccat    1980
ccagtctatt aattgttgcc gggaagctag agtaagtagt tcgccagtta atagtttgcg    2040
caacgttgtt gccattgcta caggcatcgt ggtgtcacgc tcgtcgtttg gtatggcttc    2100
attcagctcc ggttcccaac gatcaaggcg agttacatga tcccccatgt tgtgcaaaaa    2160
agcggttagc tccttcggtc ctccgatcgt tgtcagaagt aagttggccg cagtgttatc    2220
actcatggtt atggcagcac tgcataattc tcttactgtc atgccatccg taagatgctt    2280
ttctgtgact ggtgagtact caaccaagtc attctgagaa tagtgtatgc ggcgaccgag    2340
ttgctcttgc ccggcgtcaa tacgggataa taccgcgcca catagcagaa ctttaaaagt    2400
gctcatcatt ggaaaacgtt cttcggggcg aaaactctca aggatcttac cgctgttgag    2460
atccagttcg atgtaaccca ctcgtgcacc caactgatct tcagcatctt ttactttcac    2520
cagcgtttct gggtgagcaa aaacaggaag gcaaaatgcc gcaaaaaagg gaataagggc    2580
gacacggaaa tgttgaatac tcatactctt cctttttcaa tattattgaa gcatttatca    2640
gggttattgt ctcatgagcg gatacatatt tgaatgtatt tagaaaaata aacaaatagg    2700
ggttccgcgc acatttcccc gaaaagtgcc acctgacgtc taagaaacca ttattatcat    2760
gacattaacc tataaaaata ggcgtatcac gaggccctga tggctctttg cggcacccat    2820
cgttcgtaat gttccgtggc accgaggaca accctcaaga gaaatgtaa tcacactggc    2880 tcaccttcgg gtgggccttt ctgcgtttat aaggagacac tttatgttta agaaggttgg    2940
taaattcctt gcggctttgg cagccaagct agatccagct ttttgcaaaa gcctaggcct    3000
ccaaaaaagc ctcctcacta cttctggaat agctcagagg ccgaggcggc ctcggcctct    3060
gcataaataa aaaaaattag tcagccatgg ggcggagaat gggcggaact gggcggagtt    3120
aggggcggga tggggcggagt tagggggcggg actatggttg ctgactaatt gagatgcatg    3180
ctttgcatac ttctgcctgc tggggagcct ggggactttc cacacctggt tgctgactaa    3240
ttgagatgca tgctttgcat acttctgcct gctggggagc tggggacttt ccacacccct    3300
aactgacaca cattccacag ggaagctagc ttggaattaa ttccccgccc ccttccaata    3360
caaaaactaa ttagactttg agtgatcttg agcctttcct agttttttgta ttggaagggc    3420 tcgtcgccag tctcattgag aaggcatgtg cggacgatgg cttctgtcac tgcaaagggg    3480
tcacaattgg cagaggggcg gcggtcttca aagtaaccta tcttctcctg ccgagccgag    3540
aatgggagta gagccgactg cttgattccc acaccaatct cctcgccgct ctcacttcgc    3600
ctcgttctcg tggctcgtgg ccctgtccac cccgtccatc atcccgccgg ccaccgctca    3660
gagcaccttc caccatggcc acctcagcaa gttcccactt gaacaaaaac atcaagcaaa    3720
tgtacttgtg cctgccccag ggtgagaaag tccaagccat gtatatctgg gttgatggta    3780
ctggagaagg actgcgctgc aaaacccgca ccctggactg tgagcccaag tgtgtagaag    3840
```

```
agttacctga gtggaatttt gatggctcta gtacctttca gtctgagggc tccaacagtg    3900
acatgtatct cagccctgtt gccatgtttc gggacccctt ccgcagagat cccaacaagc    3960
tggtgttctg tgaagttttc aagtacaacc ggaagcctgc agagaccaat ttaaggcact    4020
cgtgtaaacg gataatggac atggtgagca accagcaccc ctggtttgga atggaacagg    4080
agtatactct gatgggaaca gatgggcacc cttttggttg gccttccaat ggctttcctg    4140
ggccccaagg tccgtattac tgtggtgtgg gcgcagacaa agcctatggc agggatatcg    4200
tggaggctca ctaccgcgcc tgcttgtatg ctggggtcaa gattacagga acaaatgctg    4260
aggtcatgcc tgcccagtgg gaactccaaa taggaccctg tgaaggaatc cgcatgggag    4320
atcatctctg ggtggcccgt ttcatcttgc atcgagtatg tgaagacttt ggggtaatag    4380
caacctttga ccccaagccc attcctggga actggaatgg tgcaggctgc cataccaact    4440
ttagcaccaa ggccatgcgg gaggagaatg gtctgaagta agtagctccc tctggaccat    4500
ctttattctc atggggtgga aggcctttgt gttaggttg ggaaaagttg gacttctcac     4560
aaactacatg ccatgctctt cgtgtttgtc ataagcctat cgttttgtac ccgttggaga    4620
agtgacagta ctctaggaat agaattacag ctgtgatatg ggaaagttgt cacgtaggtt    4680
caagcattta aggtctttta gtaagaacta aatacacata caagcaagtg ggtgacttaa    4740
ttcttactga tgggaagagg ccagtgatgg gggtcttccc atccaaaaga taattggtat    4800
tacatgttga ggactggtct gaagcacttg agacataggt cacaaggcag acacagcctg    4860
catcaagtat ttattggttt cttatggaac tcatgcctgc tcctgccctt gaaggacagg    4920
tttctagtga caaggtcaga ccctcacctt tactgcttcc accaggcaca tcgaggaggc    4980
catcgagaaa ctaagcaagc ggcaccggta ccacattcga gcctacgatc ccaagggggg    5040
gctggacaat gcccgtggtc tgactgggtt ccacgaaacg tccaacatca acgacttttc    5100
tgctggtgtc gccaatcgca gtgccagcat ccgcattccc cggactgtcg gccaggagaa    5160
gaaaggttac tttgaagacc gccgcccctc tgccaattgt gaccccttg cagtgacaga     5220
agccatcgtc cgcacatgcc ttctcaatga gactggcgac gagcccttcc aatacaaaaa    5280
ctaattagac tttgagtgat cttgagcctt tcctagttca tgccaccccg ccccagctgt    5340
ctcattgtaa ctcaaaggat ggaatatcaa cggtcttttt attcctcgtg cccagttaat    5400
ccttgctttt attggtcaga atagaggagt caagttctta atgcctatac accaacctca    5460
tttcttttct atttagcttt ctacgtgggg gtgggagggg tagggagggg taggcgaagg    5520
gaacgtaacc acatgcttca tctcatcagg aatgccatgt ccagtaggca gagctgccac    5580
agagtgggtg tatttgtgga ggaggacttt tcttcagga cagttaaaag agcaggtcca     5640
ctgcttggat tgacaattcc cctataggta gagagcttgc tagttcttca ggtaaaccaa    5700
ctttctattc caaatggaag ttaggtgagg agtagtggag gagttaatgc cctccatgaa    5760
gacagctcag tgtatcacct gagacagatg ggtagcccta ctgtaaaaga aggaaaagtt    5820
atttctgggt cctccatttta taacacaaag cagtagtatt tttatattta aatgtaaaaa    5880
caaaagttat atatatgata tgtggatata tgtgtatttc taattcagaa accatcctag    5940
ttactgggtt tgccaagttt gaagagcttg gttaacaaga aaggatctct tgagtagagg    6000
tgggggtgca gtaccaggaa aggtggttat ctggggctca gcgctttatt actatgtggg    6060
gtttcccctg cccactctgc aggagcagat gctggacagg tagcagggtg ggacaccagt    6120
gcttgccacc acctgtccct gtgcttaggc taagatgcat atgtatccac acagagttag    6180
caggatggag ttggctggtc aacttgaaca ttgttactga taggggtggg tggggtttat    6240
```

```
tttttggtgg gactagcatg tcactaaagc aggccttttg atatattaaa ttttttaaag    6300
caaaacaagt tcagctttta atcaactttg tagggtttct aactttacag aattgcctgt    6360
ttgtttcagt gtctccatcc actttgctct tggaggaacg gaggacaggc agacctggag    6420
ttaaaacatt tgtcattttg tgtcatagtg tctactttct cccagcagaa tattcctttc    6480
cttcttagga gtcctatgga gttttgtttt tgtttttttt ctattacgat aaacataccc    6540
cacctccatt ctggcttgcc ctgctgttct ctggttgttt gtgtgctgtc cgcagcaggc    6600
tgcctgtggt tttctcttgc catgacgact tctaattgcc atgtacagta tgttcagtta    6660
gataactcct cattgtaaac agactgtaac tgccagagca gcgcttataa atcaacctaa    6720
catttataag atttcctctt gacttgtttc tttgtggttg ggggaggaag aaaaaaaaaa    6780
gcgtgcagta ttttttgtt ccttcatttc ctatcaaaag aaaggggagt ggttctgttt    6840
tgtttactcg caaaataagc tagcttatct attggctttt cttttttttt ttttttttaa    6900
acgggctttt tcttgtacct ataatttggg gtaaggtgtg agagttttta tagtttttttg    6960 agacagggtc ttggtgtata cccttggctg gcctggagct aactatgtag actgggctag    7020
cctttaactt gcagttctgc tttcaattag ggtttataca tttagtcttg gcaattccta    7080
gttccacgtt taatctcttt acatttcaaa gcagtgttat ctgaagagtt caggcgcaga    7140
gtcaattcaa tagagttaca caaaaaccta aaaaacaagt tttaaatacc aagttatgtt    7200
ggcctggcca cttttcacag ctgtccacaa ctcaatgtga caaggctaca aattggatat    7260
actagaattt cctggtgatt tggaacccct gcttcatttc ccggaaccag ggcttttggt    7320
gacagtccta gcttatcaga ttatttaaaa cagttactct tcctgccctt cttcctgaga    7380
cctttgtcca gctgccatga gccatctaca cagtacttgc ttccctgttg aagtcactga    7440
aggcacatca gcccaagaca taaaggcttg tcccggattc actagcctgg tgaacttgtg    7500
gttctctgat gttttgtcct gttttgttgt gatttagtct caaattcccc agcctggttt    7560
gaaaatctgg gctcccagcc ttcaataagg aggactacag atatgtacga ctgagccttg    7620
attccagcct catgtttata cgtctgtgct cagctccctg aaggttccag tttgaaactc    7680
aataatccag gggtcagaaa gtcttgatct tatccccaca gtatggcacc aagcctggct    7740
gagccttctg acttagtctg ccctgttgct attaagcac ttttcttcac taggctaaaa    7800
ataaaaggag cttcctcctt tgccatggcg ctgtgcatga taggaaaagg tagctatcta    7860
ctagcatatt aactccactg ttttttgcttt gtgtgtttgg ttttgagga agggtctcaa    7920 ctgtgtatcc ctggctggcc tggccggatc tagcttcgtg tcaaggacgg tgaggcgcgc    7980
caatattggc tattggccat tgcatacgtt gtatccatat cataatatgt acatttatat    8040
tggctcatgt ccaacattac cgccatgttg acattgatta ttgactagtt attaatagta    8100
atcaattacg gggtcattag ttcatagccc atatatggag ttccgcgtta cataacttac    8160
ggtaaatggc ccgcctggct gaccgcccaa cgacccccgc ccattgacgt caataatgac    8220
gtatgttccc atagtaacgc caatagggac tttccattga cgtcaatggg tggagtattt    8280
acggtaaact gcccacttgg cagtacatca agtgtatcat atgccaagta cgccccctat    8340
tgacgtcaat gacggtaaat ggcccgcctg gcattatgcc cagtacatga ccttatggga    8400
ctttcctact tggcagtaca tctacgtatt agtcatcgct attaccatgg tgatgcggtt    8460
ttggcagtac atcaatgggc gtggatagcg gtttgactca cggggatttc caagtctcca    8520
ccccattgac gtcaatggga gtttgttttg gcaccaaaat caacgggact ttccaaaatg    8580
tcgtaacaac tccgccccat tgacgcaaat gggcggtagg cgtgtacggt gggaggtcta    8640
```

```
tataagcaga gctcgtttag tgaaccgtca gatcgcctgg agacgccatc cacgctgttt      8700
tgacctccat agaagacacc gggaccgatc cagcctccgc ggccgggaac ggtgcattgg      8760
aacgcggatt ccccgtgcca agagtgacgt aagtaccgcc tatagagtct ataggcccac      8820
ccccttggct tcttatgcat gctatactgt ttttggcttg gggtctatac accccgctt      8880 cctcatgtta taggtgatgg tatagcttag cctataggtg tgggttattg accattattg      8940
accactcccc tattggtgac gatactttcc attactaatc cataacatgg ctctttgcca      9000
caactctctt tattggctat atgccaatac actgtccttc agagactgac acggactctg      9060 tattttttaca ggatggggtc tcatttatta tttacaaatt cacatataca acaccaccgt     9120
ccccagtgcc cgcagttttt attaaacata acgtgggatc tccacgcgaa tctcgggtac      9180
gtgttccgga catgggctct tctccggtag cggcggagct tctacatccg agccctgctc      9240
ccatgcctcc agcgactcat ggtcgctcgg cagctccttg ctcctaacag tggaggccag      9300
acttaggcac agcacgatgc ccaccaccac cagtgtgccg cacaaggccg tggcggtagg      9360
gtatgtgtct gaaaatgagc tcggggagcg ggcttgcacc gctgacgcat ttggaagact      9420
taaggcagcg gcagaagaag atgcaggcag ctgagttgtt gtgttctgat aagagtcaga      9480
ggtaactccc gttgcggtgc tgttaacggt ggagggcagt gtagtctgag cagtactcgt      9540
tgctgccgcg cgcgccacca gacataatag ctgacagact aacagactgt tcctttccat      9600
gggtcttttc tgcagtcacc gtccttgaca cgaagcttgc cgccaccatg gtgagcaagc      9660
agatcctgaa gaacaccggc ctgcaggaga tcatgagctt caaggtgaac ctggagggcg      9720
tggtgaacaa ccacgtgttc accatggagg gctgcggcaa gggcaacatc ctgttcggca      9780
accagctggt gcagatccgc gtgaccaagg gcgccccct gcccttcgcc ttcgacatcc      9840
tgagccccgc cttccagtac ggcaaccgca ccttcaccaa gtaccccgag gacatcagcg      9900
acttcttcat ccagagcttc cccgccggct tcgtgtacga gcgcaccctg cgctacgagg      9960
acggcggcct ggtggagatc cgcagcgaca tcaacctgat cgaggagatg ttcgtgtacc     10020
gcgtggagta cagggccgc aacttcccca cgacggccc cgtgatgaag aagaccatca     10080
ccggcctgca gccagcttc gaggtggtgt acatgaacga cggcgtgctg gtgggccagg     10140
tgatcctggt gtaccgcctg aacagcggca gttctacag ctgccacatg cgcacccctga    10200 tgaagagcaa gggcgtggtg aaggacttcc ccgagtacca cttcatccag caccgcctgg     10260
agaagaccta cgtggaggac ggcggcttcg tggagcagca cgagaccgcc atcgcccagc     10320
tgaccagcct gggcaagccc ctgggcagcc tgcacgagtg ggtgtaata                10369
```

<210> SEQ ID NO 4  
<211> LENGTH: 13535  
<212> TYPE: DNA  
<213> ORGANISM: Hamster sp.  
<220> FEATURE:  
<221> NAME/KEY: misc_feature  
<223> OTHER INFORMATION: Seq. ID. No. 1: circular plasmid GS + IgG 2A  
   hot spot targetting vector pEE 15.1 hCMVp-GFP /clone 11

<400> SEQUENCE: 4

```
gaattcattg atcataatca gccataccac atttgtagag gttttacttg ctttaaaaaa       60
cctcccacac ctccccctga acctgaaaca taaaatgaat gcaattgttg ttgttaactt      120
gtttattgca gcttataatg gttacaaata aagcaatagc atcacaaatt tcacaaataa      180 agcattttt tcactgcatt ctagttgtgg tttgtccaaa ctcatcaatg tatcttatca      240
tgtctggcgg ccgcgacctg caggcgcaga actggtaggt atggaagatc cctcgagatc      300
```

```
cattgtgctg gcggtaggcg agcagcgcct gcctgaagct gcgggcattc ccagtcagaa    360
atgagcgcca gtcgtcgtcg gctctcggca ccgaagtgct atgattctcc gccagcatgg    420
cttcggccag tgcgtcgagc agcgcccgct tgttcctgaa gtgccagtaa agcgccggct    480
gctgaacccc caaccgttcc gccagtttgc gtgtcgtcag accgtctacg ccgacctcgt    540
tcaacaggtc tagggcggca cggatcactg tattcggctg caactttgtc atgcttgaca    600
ctttatcact gataaacata atatgtccac caacttatca gtgataaaga atccgcgcca    660
gcacaatgga tctcgaggtc gagggatctc tagaggatcc atattcgcga atatgccggc    720
atcaccggcg ccacaggtgc ggttgctggc gcctatatcg ccgacatcac cgatggggaa    780
gatcgggctc gccacttcgg gctcatgagc gcttgtttcg gcgtgggtat ggtggcaggc    840
ccgtggccgg gggactgttg ggcgccatct ccttgcatgc accattcctt gcggcggcgg    900
tgctcaacgg cctcaaccta ctactgggct gcttcctaat gcaggagtcg cataagggag    960
agcgtcgagt cctccgtgtt cgaagcgatc cctgtccagt ggtgtgcaca ccttcccagc   1020
tgtcctgcag tctgacctct acaccctcag cagctcagtg actgtaacct cgagcacctg   1080
gcccagccag tccatcacct gcaatgtggc ccacccggca agcagcacca aggtggacaa   1140
gaaaattggt gaggaaaaca aggggagtag aggttcacaa gtgattagtc taaggcctta   1200
gcctagctag accagccagg atcagcagcc atcaccaaaa atgggaactt ggcccagaag   1260
agaaggagat actgactgtg actccctctt ggaaacttct aactatgacc acctaccttc   1320
aaggtcatga tcctctagga tagatgtcct tggtcatttc caggatcatc ctgacctaag   1380
gccatacccca gggacaaagt ccctggtttg gtgccttttc tccttcaaac ttgagtaacc   1440
cccagccttc tctctgcaga gcccagaggg cccacaatca gccctgtcc tccatgcaaa   1500
tgcccaggta agtcactaga ccagagctcc acccgggaga atggtaagtg ctgtaaacat   1560
ccctgcacta gaggataagc catgtacaga tccatttcca tctctcctca tcagcaccta   1620
acctcttggg tggaccatcc gtcttcatct tccctccaaa gatcaaggat gtactcatga   1680
tctccctgag ccccatagtc acatgtgtgg tggtggatgt gagcgaggat gacccagatg   1740
tccagatcag ctggtttgtg aacaacgtgg aagtacacac agctcagaca caaacccata   1800
gagaggatta caacagtact ctccgggtgg tcagtgccct ccccatccag caccaggact   1860
ggatgagtgg caaggagttc aaatgcaagg tcaacaacaa agacctccca gcgcccatcg   1920
agagaaccat ctcaaaaccc aaaggtgaga gctgcagcct gactgcatgg gggctgggat   1980
gggcataagg ataaaggtct gtgtggacag ccttctgctt cagccatgac ctttgtgtat   2040
gtttctaccc tcacagggtc agtaagagct ccacaggtat atgtcttgcc tccaccagaa   2100
gaagagatga ctaagaaaca ggtcactctg acctgcatgg tcacagactt catgcctgaa   2160
gacatttacg tggagtggac caacaacggg aaaacagagc taaactacaa gaacactgaa   2220
ccagtcctgg actctgatgg ttcttacttc atgtacagca agctgagagt ggaaaagaag   2280
aactgggtgg aaagaaatag ctactcctgt tcagtggtcc acgagggtct gcacaatcac   2340
cacacgacta gagcttctc ccggactccg ggtaaatgag ctcagcaccc acaaaactct   2400
caggtccaaa gagacaccca cactcatctc catgcttccc ttgtataaat aaagcaccca   2460
ccaatgcctg ggaccatgta aaactgtcct ggttcttttcc aaggtataga gcatagctca   2520
caggctgata tttctggcca gggttggagg acagccttgt ctataggaag agaatgaggt   2580
ttttgcactg caggactcag agctcattag ttatcctgcc ttggagtgtt ggggcttggc   2640
tttaggcagt gccttttcct tgccttccta cgaaccagca gctgccatac atagagataa   2700
```

```
tcctaggaag cctcaaatgg agaaggacac aaacccacct ccctcaggct gttcctctat   2760
cccggcccca cttctttacc taggggtttc tctgagtcta ttgtggagtt acacatggcc   2820
aggggcattc cagagaccct tgtcatccat acactcaact caggcagctt tgcacaaaca   2880
aagtctgcac acccatacag atggctcact cttgcctgtg ccatgtaggg ctgaggcaca   2940
tggctcttgc tgccccaagg gagggactat tagatagcca cactcatgct gaatcctggc   3000
ccattcaaat tagcctgctg aacaccatcc agtccatata gcacatgtat ccacatgcac   3060
gtgtgcacaa aacgcattta atacactggg acaacaattc tgtgccctgc acagcaccta   3120
tatccagcaa tgtatcacca tacacacgac caaaaaaatt caatgccccac gtttctgcca   3180 tcacaaacag acacatcttt cctctctgtg gccactgcat tatatgctca acacaagacc   3240
tctgaagcca gatccatctc tggcacctcg gggtcatgct tcaaccccac atgaattatg   3300
caaaccatag ccataatggt ctgaatcact tcacactggg atgttcccaa gttcaggcaa   3360
gacgagccac aggctctgct gatgactgaa ggacagcaaa gggtcagtcc agctgtatag   3420
ccactgttga cctgggtcac aggccctgct gaccctccac cttctcctgt actgaaggaa   3480
tgaaagatga gacaagcata gagggcactt gaataatcca ggtcactctg aggtccaccc   3540
aaggcattat tggactcagg tgggaagctg agactggtgt cccagaggga aaggaaggaa   3600
agcaggcccc ggggagggtc tgctgtccca gtcaggctgg agatctctcc tctgaatcca   3660
tgcagacatg tctgcctcac agggaatctc tcccagcacc aaccatgttg ggacaaacac   3720
tgactgtcct ctctgttcag ggctagacct ggatgatgtc tgtgctgagg cccaggacgg   3780
ggagctggac ggcctctgga cgaccatcac catcttcatc agcctcttcc tgctcagcgt   3840
gtgctacagc gcctctgtca cactcttcaa ggttggcact gtctcccacc ctctgctgtg   3900
atggctacac tgaccacaaa atgtcctctc actcctcccc agatgtagta ggacgttact   3960
ttgctgcccc tactctgtcc cacacaccat ttcctccatt ccctgagcca tcccacattg   4020
ttctatgtga ctccacattg tgtcccatac agtctgccct tctgtctctc tggctgtcct   4080
gcgtgatcct gatactgtct tatgagacca aacctccttg cattccacac tagccttcat   4140
gaggttcaat gctgtcttac acacaatccc ctcagcctca ccatggctca aggtactctg   4200
tgagctatcc tcataccatc tccacctcaa ctcccacaat atctccactc tgacccctcc   4260
catacccagt ctcctacctg tatgaaggga attgaaggag agacaggtcg acctctgtct   4320
ttcccacaga ttggagggtc tgagcatggg cgtggtctct gactttctct cacttcccca   4380
caggtaaagt ggatcttctc ctctgtggtg gagctgaagc agacgatctc ccctgactac   4440
agaaacatga ttgggcaggg agcctaggcc acttcctctg ggatcagaag agcttcctag   4500
gccctgcaga agcccatcca tcctactgtg cagcctaaca gggaggccac actctagccc   4560
tatgactctc tgatcagaac tccatggtc tcctctttgg aggaccacgt gcagtgcagg   4620
ctttgcccag acctaaacac ttccacagca gtcgccagat atctaactac tccgaccacg   4680
aagaaccatc tccttccaaa ccagcactag ggatctgaga tctcagaatg tttgcctaag   4740
aagagctgga aatccaggct tcctgtgttc tgctacaagg acatcagcct ggatttgacc   4800
tggaccacac attttcatct aaatgagttt ccacaaagg acacgtttca gatccttgaa   4860
tgagacctct acatggaaga ccagagtcac tatacccaaa ggtcactctg tatccttgca   4920
ccagctatac tggacagctt ccttcctggt acttcagtga ccctggctga ggaaaggatc   4980
tgtgacctca actgtttgga gagcctctgg aagatgtagt cttctcttcc tgctaccacc   5040
aacatgctgg atctcagatg cagaatccaa tccacagaca ccactgacca cacaacctga   5100
```

```
agacaaggcc attgccacct ccacagagat gccatccaca ctctgtggag aaataaggag    5160
tgctttgtgc agcctctgca aagctctggc agggattaga gtatacacac tgagtactga    5220
ctaggtgacc aggcagaaaa acctccagga gaaggaacaa tgggggagag atgtgaacag    5280
atagttagaa aaagcatggt gtcacaggtc tgctctgtgg actgatttcc agattggacc    5340
acctacagca gaaaccatcg gttgcagtgg caatctagga ggaccaacct ggaataggag    5400
ggctgctgtg gtcaatggag agtagacctg tatctatttc tccactgcct cttatgacca    5460
ataagaagcc agagtctcca gacagaaaga aagaagaaa gaaagaaaga agaaagaaa     5520 gaaagagaga gagagagaga gagagagaga gaggaaggaa ggaaggaagg aaggaaggaa    5580
ggaaggaagg aggaggagga ggaggaggag gaggaggaga gagagagaga gagagagaga    5640
gagagagaga gagcaccagc ttttctgtga ctggaaggaa atgcttagag agcttggatc    5700
tttaaagctt cttttttcta gagaccatga atgtctttgt tctctctctc tctctctctc    5760
tctctctctc tctctctctc tctctctgtg tgtgtgtgtg tgtgtgtgtg tgtgtgtgcg    5820
tgcatgcacg ctattgtttt ggcatttgaa acaataaaac attcttttaa tattctgtat    5880
ctcatggttc cccttctgtg tggatcagcc ctaacaccca ggaacagggg acaataaaca    5940
gaccacagcc atgtacagcc ttctacctcc cttctggttc tgacctccca gaggtccctc    6000
agtgggcccc tcacagctgg gtttcttccc tggcagtgcc accaagagct caggcacctc    6060
tgagctggag gctgtcctga tgccataggc aggctatgga gcagagatga tgaccacggt    6120
ggactccagg tgagccaggc aaagcctccc atgccgaaag agaagcgtgt ggtactcact    6180
ggcctcgggc tgctacggat tcagcaaaga gcatggatcg cttcgaagcc tccaagctcg    6240
acctcgggcc gcgttgctgg cgttttttcca taggctccgc cccctgacg agcatcacaa     6300 aaatcgacgc tcaagtcaga ggtggcgaaa cccgacagga ctataaagat accaggcgtt    6360 tcccctgga agctccctcg tgcgctctcc tgttccgacc ctgccgctta ccggatacct    6420
gtccgccttt ctcccttcgg aagcgtggc gcttctcaa tgctcacgct gtaggtatct    6480
cagttcggtg taggtcgttc gctccaagct gggctgtgtg cacgaacccc ccgttcagcc    6540
cgaccgctgc gccttatccg gtaactatcg tcttgagtcc aacccggtaa gacacgactt    6600
atcgccactg gcagcagcca ctggtaacag gattagcaga gcgaggtatg taggcggtgc    6660
tacagagttc ttgaagtggt ggcctaacta cggctacact agaaggacag tatttggtat    6720
ctgcgctctg ctgaagccag ttaccttcgg aaaagagtt ggtagctctt gatccggcaa    6780
acaaaccacc gctggtagcg gtggtttttt tgtttgcaag cagcagatta cgcgcagaaa    6840
aaaaggatct caagaagatc ctttgatctt ttctacgggg tctgacgctc agtggaacga    6900
aaactcacgt taagggattt tggtcatgag attatcaaaa aggatcttca cctagatcct    6960
tttaaattaa aaatgaagtt ttaaatcaat ctaaagtata tatgagtaaa cttggtctga    7020
cagttaccaa tgcttaatca gtgaggcacc tatctcagcg atctgtctat ttcgttcatc    7080
catagttgcc tgactccccg tcgtgtagat aactacgata cgggagggct taccatctgg    7140
ccccagtgct gcaatgatac cgcgagaccc acgctcaccg gctccagatt tatcagcaat    7200
aaaccagcca gccggaaggg ccgagcgcag aagtggtcct gcaactttat ccgcctccat    7260
ccagtctatt aattgttgcc gggaagctag agtaagtagt tcgccagtta atagtttgcg    7320
caacgttgtt gccattgcta caggcatcgt ggtgtcacgc tcgtcgtttg gtatggcttc    7380
attcagctcc ggttcccaac gatcaaggcg agttacatga tcccccatgt tgtgcaaaaa    7440
agcggttagc tccttcggtc ctccgatcgt tgtcagaagt aagttggccg cagtgttatc    7500
```

```
actcatggtt atggcagcac tgcataattc tcttactgtc atgccatccg taagatgctt    7560
ttctgtgact ggtgagtact caaccaagtc attctgagaa tagtgtatgc ggcgaccgag    7620
ttgctcttgc ccggcgtcaa cacgggataa taccgcgcca catagcagaa ctttaaaagt    7680
gctcatcatt ggaaaacgtt cttcggggcg aaaactctca aggatcttac cgctgttgag    7740
atccagttcg atgtaaccca ctcgtgcacc caactgatct tcagcatctt ttactttcac    7800
cagcgtttct gggtgagcaa aaacaggaag gcaaaatgcc gcaaaaaagg gaataagggc    7860
gacacggaaa tgttgaatac tcatactctt ccttttcaa tattattgaa gcatttatca     7920
gggttattgt ctcatgagcg gatacatatt tgaatgtatt tagaaaaata acaaataggg    7980
ggttccgcgc acatttcccc gaaaagtgcc acctgacgtc taagaaacca ttattatcat    8040
gacattaacc tataaaaata ggcgtatcac gaggccctga tggctctttg cggcacccat    8100
cgttcgtaat gttccgtggc accgaggaca accctcaaga gaaaatgtaa tcacactggc    8160
tcaccttcgg gtgggccttt ctgcgtttat aaggagacac tttatgttta agaaggttgg    8220
taaattcctt gcggctttgg cagccaagct agagatccgg ctgtggaatg tgtgtcagtt    8280
agggtgtgga aagtccccag gctccccagc aggcagaagt atgcaaagca tgcatctcaa    8340
ttagtcagca accaggtgtg gaaagtcccc aggctcccca gcaggcagaa gtatgcaaag    8400
catgcatctc aattagtcag caaccatagt cccgccccta actccgccca tcccgcccct    8460
aactccgccc agttccgccc attctccgcc ccatggctga ctaatttttt ttatttatgc    8520
agaggccgag gccgcctcgg cctctgagct attccagaag tagtgaggag gcttttttgg    8580
aggcctaggc ttttgcaaaa agctagcttg ggccaccgc tcagagcacc ttccaccatg     8640
gccacctcag caagttccca cttgaacaaa acatcaagc aaatgtactt gtgcctgccc     8700
cagggtgaga aagtccaagc catgtatatc tggggttgatg gtactggaga aggactgcgc   8760
tgcaaaaccc gcaccctgga ctgtgagccc aagtgtgtag aagagttacc tgagtggaat    8820
tttgatggct ctagtacctt tcagtctgag ggctccaaca gtgacatgta tctcagccct    8880
gttgccatgt ttcgggaccc cttccgcaga gatcccaaca agctggtgtt ctgtgaagtt    8940
ttcaagtaca accggaagcc tgcagagacc aatttaaggc actcgtgtaa acggataatg    9000
gacatggtga gcaaccagca cccctggttt ggaatggaac aggagtatac tctgatggga    9060
acagatgggc acccttttgg ttggccttcc aatggctttc tgggccccca aggtccgtat    9120
tactgtggtg tgggcgcaga caaagcctat ggcagggata tcgtggaggc tcactaccgc    9180
gcctgcttgt atgctggggt caagattaca ggaacaaatg ctgaggtcat gcctgcccag    9240
tgggaactcc aaataggacc ctgtgaagga atccgcatgg gagatcatct ctgggtggcc    9300
cgtttcatct tgcatcgagt atgtgaagac tttggggtaa tagcaacctt tgaccccaag    9360
cccattcctg gaactggaaa tggtgcaggc tgccatacca actttagcac caaggccatg    9420
cgggaggaga atggtctgaa gcacatcgag gaggccatcg agaaactaag caagcggcac    9480
cggtaccaca ttcgagccta cgatcccaag gggggcctgg acaatgcccg tggtctgact    9540
gggttccacg aaaacgtcca catcaacgac ttttctgctg gtgtcgccaa tcgcagtgcc    9600
agcatccgca ttccccggac tgtcggccag gagaagaaag gttactttga agaccgcggc    9660
ccctctgcca attgtgaccc cttttgcagtg acagaagcca tcgtccgcac atgccttctc    9720
aatgagactg gcgacgagcc cttccaatac aaaaactaat tagactttga gtgatcttga    9780
gccttttccta gttcatccca ccccgcccca gagagatctt tgtgaaggaa ccttacttct    9840
gtggtgtgac ataattggac aaactaccta cagagattta aagctctaag gtaaatataa    9900
```

```
aatttttaag tgtataatgt gttaaactac tgattctaat tgtttgtgta ttttagattc    9960
caacctatgg aactgatgaa tgggagcagt ggtggaatgc ctttaatgag gaaaacctgt   10020
tttgctcaga agaaatgcca tctagtgatg atgaggctac tgctgactct caacattcta   10080
ctcctccaaa aaagaagaga aaggtagaag accccaagga ctttccttca gaattgctaa   10140
gttttttgag tcatgctgtg tttagtaata gaactcttgc ttgctttgct atttacacca   10200
caaaggaaaa agctgcactg ctatacaaga aaattatgga aaaatattct gtaacctta   10260 taagtaggca taacagttat aatcataaca tactgttttt tcttactcca cacaggcata   10320
gagtgtctgc tattaataac tatgctcaaa aattgtgtac ctttagcttt ttaatttgta   10380
aaggggttaa taaggaatat ttgatgtata gtgccttgac tagagatcat aatcagccat   10440
accacatttg tagaggtttt acttgcttta aaaaacctcc cacacctccc cctgaacctg   10500
aaacataaaa tgaatgcaat tgttgttgtt aacttgttta ttgcagctta taatggttac   10560
aaataaagca atagcatcac aaatttcaca aataaagcat ttttttcact gcattctagt   10620
tgtggtttgt ccaaactcat caatgtatct tatcatgtct ggatctctag cttcgtgtca   10680
aggacggtga ctgcagtgaa taataaaatg tgtgtttgtc cgaaatacgc gttttgagat   10740
ttctgtcgcc gactaaattc atgtcgcgcg atagtggtgt ttatcgccga tagagatggc   10800
gatattggaa aaatcgatat ttgaaaaatat ggcatattga aaatgtcgcc gatgtgagtt   10860
tctgtgtaac tgatatcgcc attttttccaa aagtgatttt tgggcatacg cgatatctgg   10920
cgatagcgct tatatcgttt acggggatg gcgatagacg actttggtga cttgggcgat   10980
tctgtgtgtc gcaaatatcg cagtttcgat ataggtgaca gacgatatga ggctatatcg   11040
ccgatagagg cgacatcaag ctggcacatg gccaatgcat atcgatctat acattgaatc   11100
aatattggcc attagccata ttattcattg gttatatagc ataaatcaat attggctatt   11160
ggccattgca tacgttgtat ccatatcata atatgtacat ttatattggc tcatgtccaa   11220
cattaccgcc atgttgacat tgattattga ctagttatta atagtaatca attacggggt   11280
cattagttca tagcccatat atggagttcc gcgttacata acttacggta aatggcccgc   11340
ctggctgacc gcccaacgac ccccgcccat tgacgtcaat aatgacgtat gttcccatag   11400
taacgccaat agggactttc cattgacgtc aatgggtgga gtatttacgg taaactgccc   11460
acttggcagt acatcaagtg tatcatatgc caagtacgcc ccctattgac gtcaatgacg   11520
gtaaatggcc cgcctggcat tatgcccagt acatgacctt atgggacttt cctacttggc   11580
agtacatcta cgtattagtc atcgctatta ccatggtgat gcggttttgg cagtacatca   11640
atgggcgtgg atagcggttt gactcacggg gatttccaag tctccacccc attgacgtca   11700
atgggagttt gttttggcac caaaatcaac gggactttcc aaaatgtcgt aacaactccg   11760
ccccattgac gcaaatgggc ggtaggcgtg tacggtggga ggtctatata agcagagctc   11820
gtttagtgaa ccgtcagatc gcctggagac gccatccacg ctgttttgac ctccatagaa   11880
gacaccggga ccgatccagc ctccgcggcc gggaacggtg cattggaacg cggattcccc   11940
gtgccaagag tgacgtaagt accgcctata gagtctatag gcccaccccc ttggcttctt   12000
atgcatgcta tactgttttt ggcttggggt ctatacaccc ccgcttcctc atgttatagg   12060
tgatggtata gcttagccta taggtgtggg ttattgacca ttattgacca ctcccctatt   12120
ggtgacgata ctttccatta ctaatccata acatggctct ttgccacaac tctctttatt   12180
ggctatatgc caatacactg tccttcgaga actgacacgg actctgtatt tttacaggat   12240
ggggtctcat ttattattta caaattcaca tatacaacac caccgtcccc agtgcccgca   12300
```

```
gtttttatta aacataacgt gggatctcca cgcgaatctc gggtacgtgt tccggacatg    12360
ggctcttctc cggtagcggc ggagcttcta catccgagcc ctgctcccat gcctccagcg    12420
actcatggtc gctcggcagc tccttgctcc taacagtgga ggccagactt aggcacagca    12480
cgatgcccac caccaccagt gtgccgcaca aggccgtggc ggtagggtat gtgtctgaaa    12540
atgagctcgg ggagcgggct tgcaccgctg acgcatttgg aagacttaag gcagcggcag    12600
aagaagatgc aggcagctga gttgttgtgt tctgataaga gtcagaggta actcccgttg    12660
cggtgctgtt aacggtggag ggcagtgtag tctgagcagt actcgttgct gccgcgcgcg    12720
ccaccagaca taatagctga cagactaaca gactgttcct ttccatgggt cttttctgca    12780
gtcaccgtcc ttgacacgaa gcttgccgcc accatggtga gcaagcagat cctgaagaac    12840
accggcctgc aggagatcat gagcttcaag gtgaacctgg agggcgtggt gaacaaccac    12900
gtgttcacca tggagggctg cggcaagggc aacatcctgt tcggcaacca gctggtgcag    12960
atccgcgtga ccaagggcgc cccctgccc ttcgccttcg acatcctgag ccccgccttc    13020
cagtacggca accgcacctt caccaagtac cccgaggaca tcagcgactt cttcatccag    13080
agcttccccg ccggcttcgt gtacgagcgc accctgcgct acgaggacgg cggcctggtg    13140
gagatccgca gcgacatcaa cctgatcgag gagatgttcg tgtaccgcgt ggagtacaag    13200
ggccgcaact tccccaacga cggccccgtg atgaagaaga ccatcaccgg cctgcagccc    13260
agcttcgagg tggtgtacat gaacgacggc gtgctggtgg gccaggtgat cctggtgtac    13320
cgcctgaaca gcggcaagtt ctacagctgc cacatgcgca ccctgatgaa gagcaagggc    13380
gtggtgaagg acttccccga gtaccacttc atccagcacc gcctggagaa gacctacgtg    13440
gaggacggcg gcttcgtgga gcagcacgag accgccatcg cccagctgac cagcctgggc    13500
aagcccctgg gcagcctgca cgagtgggtg taata                              13535
```

METHOD OF EXPRESSING RECOMBINANT PROTEIN IN CHO CELLS

Figure 1:
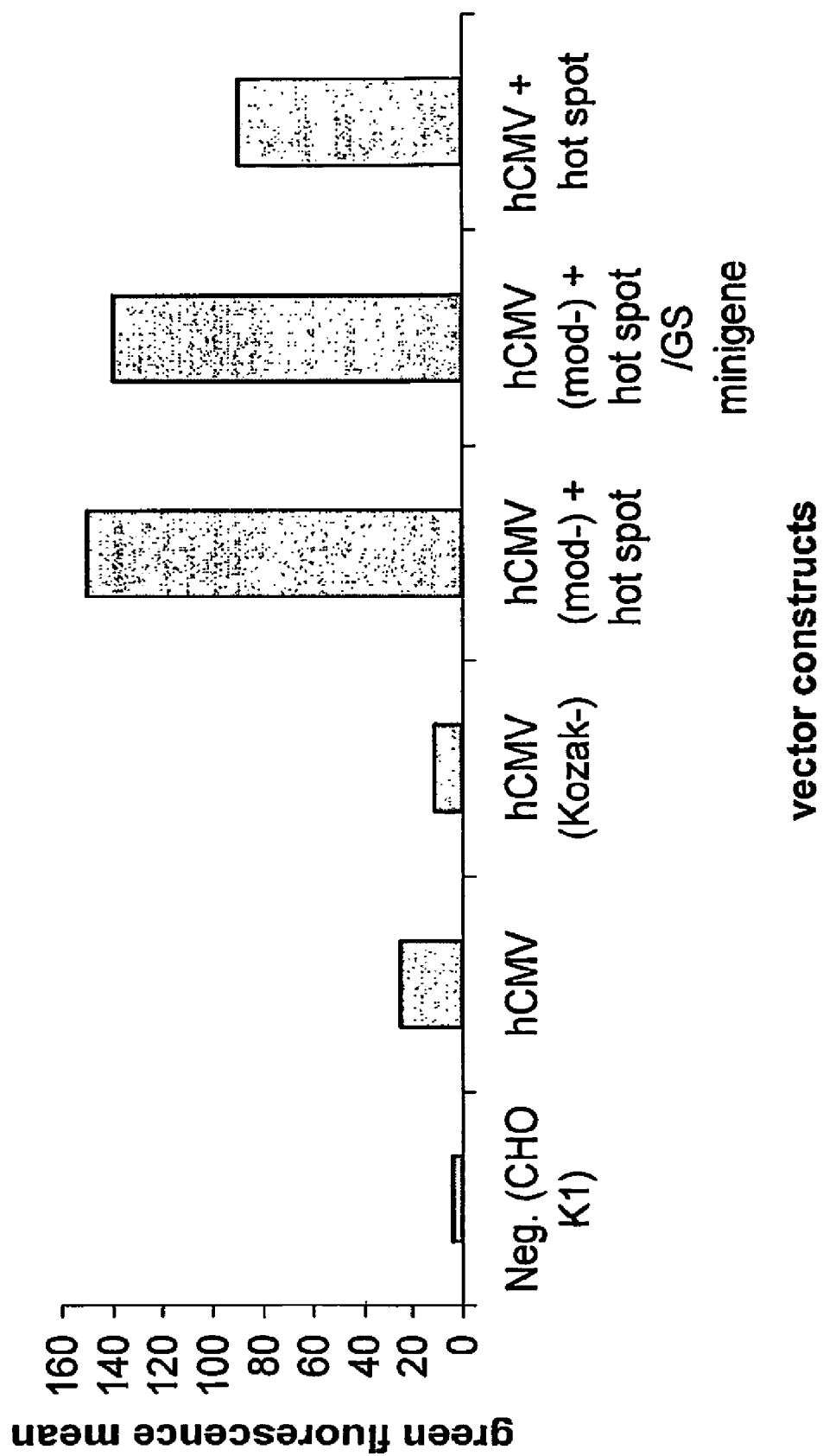

This application is a divisional of U.S. application Ser. No. 10/521,768, filed Jan. 19, 2005 now abandoned, which is a 371 U.S. national phase of international application PCT/EP2003/007946 filed 21 Jul. 2003 which designated the U.S. and claims benefit of GB 0216648.6, dated 19 Jul. 2002, the entire content of each of which are hereby incorporated by reference.

The present invention relates to a method for expressing a recombinant product gene in a CHO cell line as well as to recombinant CHO host cells and to novel expression vector constructs.

The Chinese Hamster ovary cell (CHO) mammalian expression system is widely used in production of recombinant protein. Apart from lymphoid cell lines such as hybridoma cell lines, it is one of the few cell types allowing for simple and efficient high-density suspension batch culture of animal cell. Furthermore, they allow for very high product yields and are comparatively robust to metabolic stresses whereas lymphoid cells are more difficult to culture at an industrial scale. Given considerable cost of production, it is of utmost importance to maximize the yield of recombinant protein per bioreactor run. Choice of culture medium composition and bioreactor design and operation are parameters that impact yield and may be quite complex to optimize. More predictably, increases in the strength or transcriptional activity of the promoter controlling expression of product protein enhance yield. Incremental increases at the single cell level will translate into considerable improvements of product yield in high-density batch or fed-batch culture showing stationary phase gene expression at cell densities in the range of $10^6$ to $10^7$ cells/ml.

U.S. Pat. No. 5,866,359 describes a method of enhancing expression from an already strong hCMV promoter in CHO and NSO cells by co-expressing adenoviral E1A protein from a weak promoter. E1A is a multifunctional transcription factor which may act on cell cycle regulation and has both independent transcriptional activating and repressing functional domains. The finetuning of E1A expression to appropriate low level expression is crucial for success of the co-expression approach in order to achieve the ideal balance in between gene transactivation whilst avoiding any negative impact on cell cycle progression. As a disadvantage, apart from careful choice of the promoter driving E1A expression, this system blocks part of the protein synthesis capacity of the cell with E1A expression rather than expressing the recombinant protein of interest.

WO 95/17516 describes use of the murine immunoglobulin gamma 2A locus for targeting an expression vector construct to a highly active gene locus in lymphoid cells of the B-cell lineage, e.g. widely used NSO myeloma cells. NSO cells essentially are a tumor cell line of murine plasma or B-cells. Only in B-cells, the chromatin harboring the immunoglobulin loci is in its fully active, open state, allowing for high transcriptional activity of native immunoglobulin promoters or recombinant expression constructs integrated into those gene loci.

As a disadvantage, due to the principle of homologous recombination, the targeting sequence will target efficiently in murine cell lines only matching the sequence of the gamma 2 A targeting sequence harboring a recombinatorial hot spot; for high level expression, the gamma 2A locus region must be a transcriptionally active genomic region, limiting its effectiveness for homologous recombination to B-cell types.

It is an object of the present invention to devise another expression system for CHO protein expression in biotechnology which allows for enhanced expression from a standard promoter. According to the present invention, this aim is surprisingly achieved by equipping a gene expression vector for CHO cells with a gene targeting sequence having been originally devised for homologous recombination in murine B-cells.

Figure 2:
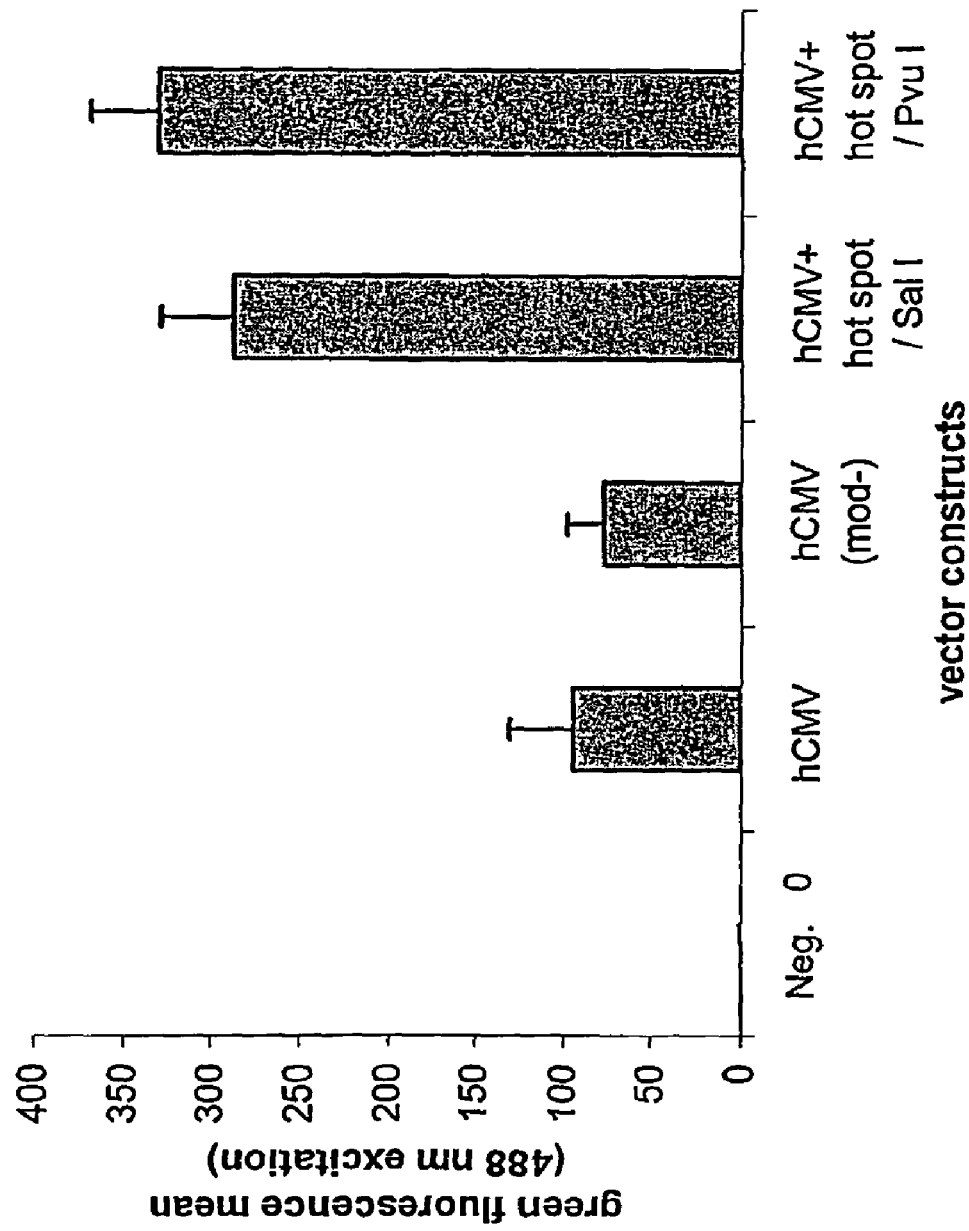

Possible embodiments of the invention are shown in the figures. What is shown is:

FIG. 1 Relative expression levels of green fluorescent protein (GFP) from hCMV promoter and hCMV promoter in the presence of the IgG 2A hot spot sequence in transient transfection of CHO-K1 cells FIG. 2 Relative GFP expression levels from hCMV promoter and hCMV promoter in the presence of the IgG 2A hot spot sequence in stably transfected CHO-K1 cells.

Figure 3:
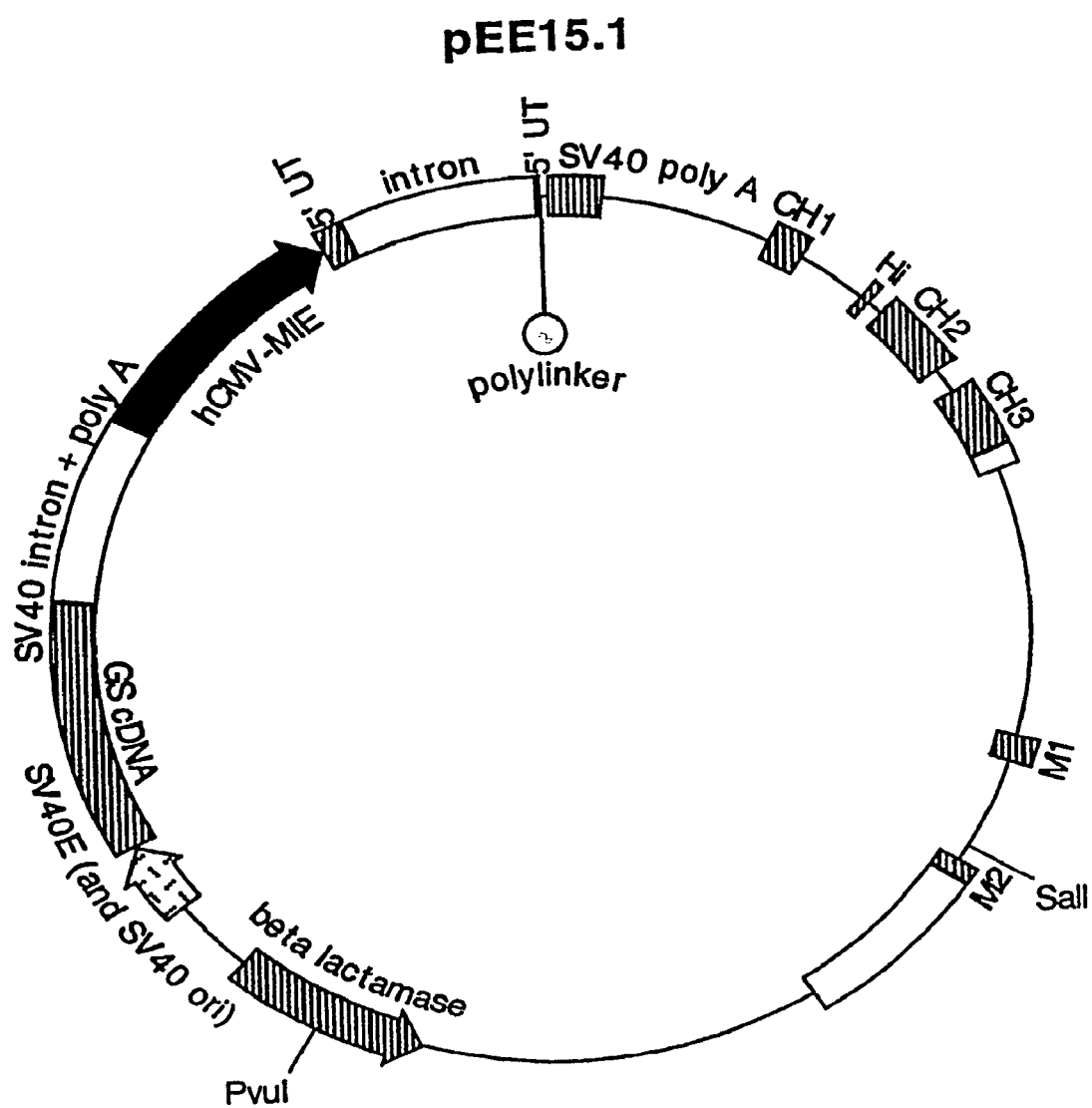

FIG. 3 Plasmid map of hCMV-MIE expression vector carrying IgG 2A targeting sequence According to the present invention, a DNA sequence for expression of a recombinant gene in a mammalian cell comprises a recombinant product gene and a promoter for expressing the recombinant product gene, preferably a CMV promoter, and further comprises a murine immunoglobulin gamma 2A locus DNA sequence or fragments or sequence variants thereof capable of enhancing expression from the promoter. According to the present invention, such a DNA sequence is useful expression vector construct for expression of recombinant product gene in CHO cells.

According to the present invention, the method of expressing a recombinant protein comprises the steps of
   a. culturing a CHO cell transfected with an expression vector comprising a promoter active in CHO cells driving expression of a recombinant product protein and further comprising the murine IgG 2A gene locus DNA or a DNA sequence variant or DNA fragment thereof which is enhancing activity of said promoter, and
   b. harvesting the product protein A recombinant product gene according to the present invention is the product protein that is sought to be expressed and harvested in high amount. It may be any protein of interest, e.g. therapeutic proteins such as interleukins or enzymes or subunits of multimeric proteins such as antibodies or fragments thereof. The recombinant product gene may include a signal sequence coding sequence portion allowing secretion of the once expressed polypeptide from the host producer cell. In a further preferred embodiment of the present invention, the product protein is a secreted protein. More preferably, the first or product protein is an antibody or engineered antibody or a fragment thereof, most preferably it is an Immunoglobulin G (IgG) antibody.

The DNA sequence of the murine immunoglobulin gamma 2A gene locus (IgG 2A) has originally been devised in WO 95/17516 for use as a genomic targeting sequence for generating stably recombinant lymphoid B-cell lines that show high expression of the recombinant gene product. B lymphocytes or plasma cells normally express extremely high levels of immunoglobulin RNA from the Ig heavy chain locus, probably due to cell-type specific enhancer/transcription factor activity and open chromatin structure. The preferred murine immunoglobulin gamma 2A gene sequence of the present invention is the same as the targeting sequence used in WO 95/17516. It is a 5.1 kb BamHI genomic fragment which includes all of the coding region of murine Ig gamma 2A except the most 5' part of the CH1 exon (Yamawaki-Kataoka, Y. et al., Proc. Natl. Acad. Sci. U.S.A. (1982) 79: 2623-2627; Hall, B. et al., Molecular Immunology (1989) 26:819-826;

Yamawaki-Kataoka, Y. et al., Nucleic Acid Research (1981) 9: 1365-1381). According to the present invention, promotion of site-directed, homologous recombination is not the relevant property of the immunoglobulin gamma 2A gene sequence (IgG 2A). Accordingly, any sequence variant of said IgG 2A gene sequence or sequence fragment or variant sequence fragment that is functional in or capable of enhancing recombinant product gene expression from the promoter, preferably from a hCMV promoter as set forth below, both under condition of transient or stable expression in CHO cells is also encompassed by the present invention.

Such 'functional' variants encompass e.g. base insertions, deletions or point mutations and be generated by methods well-known in the art, e.g. by primer-directed PCR, 'error-prone' PCR, 'gene-shuffling' termed PCR-reassembly of overlapping DNA fragments or by in-vivo random mutagenesis of bacterial clones followed by library transfection and functional selection in CHO cells. For instance, random mutagenesis can be achieved by alkylating chemicals or UV-irradiations as described in Miller, J., Experiments in Molecular Genetics, Cold Spring Harbor Laboratory 1972). Optionally, a natural mutator-strain of a host bacterium may be used.

Preferably, such variant sequence or sequence fragment is at least 65%, more preferably 75%, most preferably 90% homologous in DNA sequence to the corresponding part of the natural murine immunoglobulin gamma 2A gene locus. For instance, it is possible to insert a Sal I restriction site at the naturally occurring Stu I site present 39 bp upstream of membrane exon 2 (M2) to provide a unique site for linearization within the murine immunoglobulin gamma 2A sequence; such sequence variant was originally devised for site-specific recombination targeting, but can as well be employed in the context of the present invention.

A 'promoter' is defined as a DNA sequence that directs RNA polymerase to bind to DNA and initiates RNA synthesis. According to the present invention, it is a promoter that is active in CHO cells. Such a promoter preferably is a strong promoter. A strong promoter is one which causes mRNAs to be initiated at high frequency equal to or higher than that of hCMV core promoter/enhancer fragment (described in U.S. Pat. No. 5,168,062) in CHO-KI cells. Such promoter may be a cell-type dependent strong promoter, as are cited in U.S. Pat. No. 5,589,392, or preferably is a ubiquitously active strong promoter, more preferably a constitutively active viral promoter such as e.g. early and late promoters of the SV40 virus, the immediate early promoter of the human cytomegalovirus (hCMV) or of murine cytomegalovirus (mCMV), the thymidine kinase promoter (TK) of Herpes Simplex virus or the Rous Sarcoma Virus long terminal repeat promoter (RS-LTR), more preferably it is the hCMV-MIE promoter as defined by the 2.1 kb Pst I fragment described in U.S. Pat. No. 5,385,839 and/or EP-323 997-A1 or a functional part thereof having promoter activity. The hCMV promoter construct harboring the complete first functional intron of the major immediate early (MIE) gene of hCMV, as set forth in EP-323 997-A1, is a particularly preferred embodiment of the present invention.

Preferably a hCMV promoter employed in the present invention lacks the 'modulator' sequence part in the upstream/enhancer portion of the promoter. The 'modulator' sequence has been found to be detrimental to hCMV promoter activity in CHO cells and stretches from position −750 to position −1150 relative to the MIE transcription start site (Meier et al., 1996, Intervirology 39: 331-342, Regulation of hCMV immediate-early gene expression), in particular in transient transfection. Without the modulator sequence, the enhancing effect of the presence of the IgG 2A host spot sequence on (modulator negative or mod− for short) hCMV promoter is even more pronounced.

A transient transfection is characterised by non-appliance of any selection pressure for a vector borne selection marker. A pool or batch of cells originating from a transient transfection is a pooled cell population that comprises cells which have taken up and do express and cells that have not taken up the foreign DNA. Cells that express the foreign expression cassette do usually not have integrated the transfected DNA into their genome yet and tend to lose the foreign DNA and to overgrow transfected cells in the population upon culture of the transiently transfected cell pool. Therefore expression is strongest in the period immediately following transfection and decreases with time. Preferably, a transient transfectant according to the present invention is understood as a cell that is maintained in cell culture in the absence of selection pressure up to a time of 90 hours post transfection.

Preferably, a transfected CHO host cell according to the present invention is a stably transfected host cell, in particular in combination with a hCMV promoter as set forth above. Stable transfection means that newly introduced foreign DNA is becoming incorporated into genomic DNA, usually by random, non-homologous recombination events; in case of a vector sequence, stable transfection according to the present invention may result in loss of vector sequence parts not directly related to expression of the recombinant product gene, such as e.g. bacterial copy number control regions rendered superfluous upon genomic integration. A transfected host cell has integrated at least part or different parts of the expression vector into the genome. Likewise, transfection of CHO cells with two or several DNA fragments giving rise at least in vivo to functional equivalents of the essential elements of the expression vector of the invention, namely the product gene under control of a suitable promoter and the hot spot IgG 2A sequence, is contained in the definition of such transfected host cells. In vivo assembly of functional DNA sequences after transfection of fragmented DNA is described e.g. in WO 99/53046. It is possible that such stable integration gives rise, upon exposure to further selection pressure for gene amplification, to double minute chromosomes in CHO cells. This is comprised in the present meaning of 'stable'. Upon random genomic integration of the expression vector of the present invention in CHO, the presence of the targeting sequence enhances promoter activity for expression of the recombinant product protein. Such effect has not been observed nor could it have been anticipated upon homologous gene targeting in mature murine B-cell lines including plasmacytoma/myeloma cell lines; there, the IgG 2A targeting sequence served solely to increase the frequency of high-yielding homologous integrants since the IgG 2A locus proved to be a recombinatorial 'hot spot'. As said before, the chromatin of the immunoglobulin genomic region is in an open, highly active state in suitably targeted B-cell lines.

'Expression vectors' are defined herein as DNA sequences that are required for transcription and the translation of their mRNAs in an appropriate mammalian host cell line after transfection with vector. An appropriately constructed expression vector should usually contain: at least one expressible marker selectable in animal cells, a limited number of useful restriction sites for insertion of the expression cassette for the recombinant product gene under control of an upstream promoter region. Where used in particular for transient/episomal expression only, it may further comprise an origin of replication such as origin of Epstein Barr Virus (EBV) or SV40 virus for autonomous replication/episomal maintenance in eukaryotic host cells but may be devoid of a selectable marker. Expression vectors are e.g., but are not limited to, linear DNA fragments, DNA fragments encompassing nuclear targeting sequences or are specially optimized for interaction with transfection reagents, animal viruses or suitable plasmids that can be shuttled and produced in bacteria. Any selection marker commonly employed such as thymidine kinase (tk), dihydrofolate reductase (DHFR) or glutamine synthetase (GS) may be used. In a preferred embodiment, an expressible GS selection marker is employed (Bebbington et al., 1992, High-level expression of a recombinant antibody from myeloma cells using a glutamine synthetase gene as an amplifiable selectable marker, Bio/Technology 10:169-175; Cockett et al., 1990, High level expression of tissue inhibitor of metalloproteinases in Chinese Hamster Ovary (CHO) cells using Glutamine synthetase gene amplification, Bio/Technology 8: 662-667). The GS-system is one of only two systems that are of particular importance for the production of therapeutic proteins. In comparison to the dihydrofolate reductase (DHFR) system, the GS system offers a large time advantage during development because highly productive cell lines can often be created from the initial transfectant thus avoiding the need for multiple rounds of selection in the presence of increasing concentrations of selective agent in order to achieve gene amplification (Brown et al., 1992, Process development for the production of recombinant antibodies using the glutamine synthetase (GS) system, Cytotechnology 9:231-236). It goes without saying that equivalent to a second transcription unit for expression of the marker gene, an expression unit could use a monocistronic expression cassette both for the product gene and the marker gene by employing e.g. internal ribosome entry sites as is routinely employed in the art. Vice versa, it goes without saying that the hot spot IgG 2A sequence of the present invention and the expression cassette for the product protein comprising a promoter and/or marker cassette are not required to work in cis on a single expression vector; the elements can be well carried on separate co-transfected vectors or DNA fragments which may then be chromosomally integrated at a single, concatemeric integration site.

A further object of the present invention are CHO host cells transfected with the DNA sequences of the present invention. Further objects are a method for transfection of such host cells and a method for expression of the recombinant product gene in such host cells. The explanations and references made to preferred embodiments in the present specification of the invention relate likewise to all these further objects of the present invention. It is to be noted that a host cell transfected with the DNA sequence or vector of the present invention is to be construed as being a transiently or stably transfected cell line. Any transfection technique such as those well-known in the art, e.g. electroporation, Ca-phosphate precipitation, DEAE-dextran transfection, lipofection, can be employed according to the present invention if appropriate for a given host cell type.

A suitable host cell line can be any Chinese hamster ovary (CHO) cell line (Puck et al., 1958, J. Exp. Med. 108: 945-955). The term 'host cell' refers to cells capable of growth in culture and expressing a desired protein recombinant product protein. Suitable cell lines can be e.g. CHO K1 (ATCC CCL-61), CHO pro3−, CHO DG44, CHO P12 or the dhfr-CHO cell line DUK-BII (Chassin et al., PNAS 77, 1980, 4216-4220) or DUXB11 (Simonsen et al., PNAS 80, 1983, 2495-2499). In CHO cells, the immunoglobulin gene loci are inactive and the chromatin is therefore in a densely packaged or closed state. Thus, any gene construct integrated in the immunoglobulin loci could not give rise to high-level expression of recombinant protein due to the specific state of chromatin, unless it would itself comprise flanking locus control regions promoting opening of the chromatin on both sides of the expression cassette. Further, immunoglobulin gene sequence, and in particular the intron portions of it, show considerably divergence amongst species, e.g. from mouse to hamster. The promoter or enhancer elements of immunoglobline loci are both species and tissue specific and should be active in B-cells only. The murine IgG 2A sequence of the present invention enhances gene expression in CHO cells also in the absence of any natural immunoglobulin promoter that is giving rise to full-length transcripts coding for complete IgG heavy chain. Preferably, the IgG 2A sequence of the present invention is devoid of such promoter. Surprisingly, the murine IgG 2 A targeting sequence even improved gene expression in CHO cells upon transient transfection of CHO cells with expression vectors according to the present invention (FIG. 1); such transient expression is a further preferred embodiment of a method according to the present invention. In transient expression assays which are commonly taking place about 20-50 hours post transfection, the transfected vectors are maintained as episomal elements and are not yet integrated into the genome.

Suitable media and culture methods for mammalian cell lines are well-known in the art, as described in U.S. Pat. No. 5,633,162 for instance. Examples of standard cell culture media for laboratory flask or low density cell culture and being adapted to the needs of particular cell types are for instance: Roswell Park Memorial Institute (RPMI) 1640 medium (Morre, G., The Journal of the American Medical Association, 199, p. 519 f. 1967), L-15 medium (Leibovitz, A. et al., Amer. J. of Hygiene, 78, 1 p. 173 ff, 1963), Dulbecco's modified Eagle's medium (DMEM), Eagle's minimal essential medium (MEM), Ham's F12 medium (Ham, R. et al., Proc. Natl. Acad. Sc. 53, p 288 ff. 1965) or Iscoves' modified DMEM lacking albumin, transferrin and lecithin (Iscoves et al., J. Exp. med. 1, p. 923 ff., 1978). For instance, Ham's F10 or F12 media were specially designed for CHO cell culture. Other media specially adapted to CHO cell culture are described in EP-481 791. It is known that such culture media can be supplemented with fetal bovine serum (FBS, also called fetal calf serum FCS), the latter providing a natural source of a plethora of hormones and growth factors. The cell culture of mammalian cells is nowadays a routine operation well-described in scientific textbooks and manuals, it is covered in detail e.g. in R. Ian Fresney, Culture of Animal cells, a manual, 4$^{th}$ edition, Wiley-Liss/N.Y., 2000.

Preferably, the cell culture medium according to the present invention is devoid of fetal calf serum (FCS or FBS), which then is being termed 'serum-free'. Cells in serum-free medium generally require insulin and transferrin in a serum-free medium for optimal growth. Transferrin may at least partially be substituted by non-peptide chelating agents or siderophores such as tropolone as described in WO 94/02592 or increased levels of a source of an organic iron favorably in conjunction with antioxidants such as vitamin C. Most cell lines require one or more of synthetic growth factors (comprising recombinant polypeptides), including e.g. epidermal growth factor (EGF), fibroblast growth factor (FGF), insulin like growth factors I and II (IGFI, IGFII), etc. Other classes of factors which may be necessary include: prostaglandins, transport and binding proteins (e.g. ceruloplasmin, high and low density lipoproteins, bovine serum albumin (BSA)), hormones, including steroid-hormones, and fatty acids. Polypeptide factor testing is best done in a stepwise fashion testing new polypeptide factors in the presence of those found to be growth stimulatory. Those growth factors are synthetic or recombinant. There a several methodological approaches well-known in animal cell culture, an exemplary being described in the following. The initial step is to obtain conditions where the cells will survive and/or grow slowly for 3-6 days after transfer from serum-supplemented culture medium. In most cell types, this is at least in part a function of inoculum density. Once the optimal hormone/growth factor/polypeptide supplement is found, the inoculum density required for survival will decrease. In a more preferred embodiment, the cell culture medium is protein-free, that is free both of fetal serum and individual protein growth factor supplements or other protein such as recombinant transferrin.

A possible embodiment of one method of the present invention, namely expression and harvest of the recombinant product protein, is high-density growth of the animal host cells e.g. in an industrial fed-batch bioreactor. Conventional downstream processing may then be applied. Consequently, a high-density growth culture medium has to be employed. Such high-density growth media can usually be supplemented with nutrients such as all amino acids, energy sources such as glucose in the range given above, inorganic salts, vitamins, trace elements (defined as inorganic compounds usually present at final concentrations in the micromolar range), buffers, the four nucleosides or their corresponding nucleotides, antioxidants such as Glutathione (reduced), Vitamin C and other components such as important membrane lipids, e.g. cholesterol or phosphatidylcholine or lipid precursors, e.g. choline or inositol. A high-density medium will be enriched in most or all of these compounds, and will, except for the inorganic salts based on which the osmolarity of the essentially isotonic medium is regulated, comprise them in higher amounts (fortified) than the aforementioned standard media as can be incurred from GB2251 249 in comparison with RPMI 1640. Preferably, a high-density culture medium according to the present invention is balancedly fortified in that all amino acids except for Tryptophane are in excess of 75 mg/l culture medium. Preferably, in conjunction with the general amino acid requirement, Glutamine and/or Asparagine are in excess of 1 g/l, more preferably of 2 g/l of high-density culture medium. In the context of the present invention, high-density cell culture is defined as a population of animal cells having temporarily a density of viable cells of at least or in excess of $10^5$ cells/ml, preferably of at least or in excess of $10^6$ cells/ml, and which population has been continuously grown from a single cell or inoculum of lower viable cell density in a cell culture medium in a constant or increasing culture volume.

In a further preferred embodiment, the fed-batch culture is a culture system wherein at least Glutamine, optionally with one or several other amino acids, preferably glycine, is fed to the cell culture as described in GB2251249 for maintaining their concentration in the medium, apart from controlling glucose concentration by separate feed. More preferably, the feed of glutamine and optionally one or several other amino acids is combined with feeding one or more energy sources such as glucose to the cell culture as described in EP-229 809-A. Feed is usually initiated at 25-60 hours after start of the culture; for instance, it is useful to start feed when cells have reached a density of about $10^6$ cells/ml. It is well known in the art that in cultured animal cells, 'glutaminolysis' (McKeehan et al., 1984, Glutaminolysis in animal cells, in: Carbohydrate Metabolism in Cultured Cells, ed. M. J. Morgan, Plenum Press, New York, pp. 11-150) may become an important source of energy during growth phase. The total glutamine and/or asparagine feed (for substitution of glutamine by asparagine, see Kurano, N. et al., 1990, J. Biotechnology 15, 113-128) is usually in the range from 0.5 to 10 g per l, preferably from 1 to 2 g per l culture volume; other amino acids that can be present in the feed are from 10 to 300 mg total feed per liter of culture, in particular glycine, lysine, arginine, valine, isoleucine and leucine are usually fed at higher amounts of at least 150 to 200 mg as compared to the other amino acids. The feed can be added as shot-addition or as continuously pumped feed, preferably the feed is almost continuously pumped into the bioreactor. It goes without saying that the pH is carefully controlled during fed-batch cultivation in a bioreactor at an approximately physiological pH optimal for a given cell line by addition of base or buffer. When glucose is used as an energy source the total glucose feed is usually from 1 to 10, preferably from 3 to 6 grams per liter of the culture. Apart from inclusion of amino acids, the feed preferably comprises a low amount of choline in the range of 5 to 20 mg per liter of culture. More preferably, such feed of choline is combined with supplementation of ethanolamine essentially as described in U.S. Pat. No. 6,048,728, in particular in combination with feeding glutamine. It goes without saying that upon use of the GS-marker system, lower amounts of glutamine will be required as compared to a non-GS expression system since accumulation of excessive glutamine in addition to the endogenously produced would give rise to ammonia production and concomitant toxicity. For GS, glutamine in the medium or feed is mostly substituted by its equivalents and/or precursors, that is asparagine and/or glutamate.

It is a further, independent object of the present invention to devise an expression vector comprising at least a (first) transcription unit for a product gene, giving rise to product protein upon expression in a host cell, and which transcription unit is under the control of the mouse Cytomegalovirus promoter (mCMV promoter), and further comprising a second transcription unit comprising a glutamine synthetase (GS) marker gene. Such a product gene, or gene of interest (GOI) as it may be termed, can be e.g. an immunoglobulin coding sequence. A glutamine synthetase marker gene is any enzymatically active GS coding sequence, be it a natural gene sequence or a variant thereof. The above definitions of 'functional variant' as set forth above apply here as well including the preferred ranges of sequence homology. Preferably, the GS marker gene is a mammalian GS marker gene or derived thereof. Surprisingly, such expression vector allows for much higher transfection rates upon transfection in CHO cells than does e.g. an expression vector in which the first transcription unit harboring the gene of interest is under control of the hCMV promoter. This despite the fact that in CHO cells, transcriptional activity of the mCMV promoter is much higher than that of hCMV promoter; usually it is believed that upon transfection, higher metabolic load reduces clonal survival upon transfection, resulting in lower numbers of transfectants. Thus the effect can not be correlated in an obvious manner with the amount or unexpected toxicity of product protein expressed, the latter possibly adversely affecting growth of transfectants. Indeed, the finding is the very opposite of any expectation of a skilled person.

Further objects according to the present invention are animal host cells, in particular CHO cells, transfected with such an expression vector which vector can be maintained episomally or can be stably integrated in the genome and a respective transfection method. Likewise, transfection of animal cells, in particular CHO cells, with two or more gene fragments giving rise in-vivo to functional equivalents of the transcription units of the present object of the invention, is within the definition of such transfected host cells. Preferably, said host cells are stably transfected cells, meaning that the first and second transcription unit are chromosomally integrated.

A further object is the use of mCMV promoter to enhance transfection rate in CHO cells, preferably when using an expression vector comprising at least a first transcription unit for a product gene which first unit is giving rise to product protein upon expression in a host cell and which first transcription unit is further under the control of the mouse Cytomegalovirus promoter (mCMV promoter), and further comprising a second transcription unit comprising a glutamine synthetase (GS) marker gene. It may also be possible to transfect the first and second expression borne on different vectors, or as isolated gene fragments harboring individual expression units. Further, it may be possible to transfect a CHO cell that is already recombinant for and expresses GS with a first transcription unit harboring mCMV. According to the present invention, 'enhancing transfection rate' is defining by comparing transfection rate in the presence of the mCMV promoter and expression vector according to the present invention with the transfection rate of the same expression vector and host cell under identical transfection and cell culture conditions except that in the expression vector, the mCMV promoter is substituted to the hCMV-first intron enhancer/promoter construct as defined in U.S. Pat. No. 5,658,759 and as set forth e.g. in sequence ID. No. 3 of the present invention. This hCMV-intron MIE-promoter construct, for a given identical product gene, serves as a standard for determining the claimed effect of enhanced transfection rates. Preferably, use of mCMV promoter results in at least 10-times enhanced transfection rate.

All relevant definitions given further above apply likewise to the present, independent objects of the invention. It must be stressed that the present object of the invention does not require the presence of the murine IgG 2A targeting sequence as a prerequisite.

Murine cytomegalovirus (mCMV) is a member of the highly diverse group of herpesviridae. Even amongst cytomegaloviruses of different host species there can be wide variation. For example, mCMV differs considerably from the human cytomegalovirus (hCMV) with respect to biological properties, immediate early (IE) gene organization, and overall nucleotide sequence. The 235-kbp genome of mCMV also lacks large internal and terminal repeat characteristics of hCMV. Accordingly, no isomeric forms of the MCMV genome exist (Ebeling, A. et al., (1983), J. Virol. 47, 421-433; Mercer, J. A. et al., (1983), Virology 129, 94-106). According to the present invention, it is possible to employ the promoter region essentially corresponding to a large approx. 2.1 kb PstI fragment described in U.S. Pat. No. 4,968,615 or any functional fragment thereof. In a more preferred embodiment, the mCMV promoter fragment employed comprises the transcription start site (+0) and extends upstream to about position −500. Surprisingly, such fragment has been found to promote stronger expression than a promoter cassette extending 800 bp further upstream beyond position −500. In a most preferred embodiment, a core promoter region is employed that extends from the transcription start site upstream but to the Xho I restriction site at about position −150 from the natural transcription start site or even extending but to position −100 upstream from the natural transcriptions start site. It goes without saying that the transcription start site might be engineered in order to comprise a suitable restriction site for insertion of the recombinant product gene.

According to the present invention, it is also possible that the first transcription unit that is under control of the mCMV promoter harbors at least one intron sequence. Such measure is well-known in the art for stabilising RNA transcripts and for promoting efficient protein synthesis from the corresponding mRNA. For efficient protein synthesis without having regard to the claimed effect on transfection rate, it is however not advisable to include the first, natural intron of mCMV in the mCMV promoter construct. In contrast to the situation with hCMV promoter (cf. U.S. Pat. No. 5,591,639), such natural first intron of mCMV was found to decrease expression of a recombinant gene from the mCMV promoter and is therefore excluded in a further preferred embodiment.

Examples of preferred, possible embodiments of GS marker gene cassettes are given in the sequence listings. Seq IDs No. 1 (pEE 15.1 hCMV/GFP+hot spot)+2 (pEE 14.4 hCMV/GFP) give examples of suitable GS-gene cassettes that are expressed from the SV40 (early and late, respectively) promoter, a weak to medium level promoter, further comprising an expression cassette for GFP (Green fluorescent protein) that is under control of the hCMV promoter. Seq. ID No. 1 describes a GS cDNA sequence described in more detail in the figure legend of FIG. 3, under control of the SV40 early promoter. Seq. ID No. 2 specifies an artificial GS-minigene cassette comprising an intron that is under control of the SV40 late promoter. CHO cells are not naturally glutamine auxothropic, therefore selection schemes as e.g. described in Cockett et al., 1990, High level expression of tissue inhibitor of metalloproteinases in Chinese Hamster Ovary (CHO) cells using Glutamine synthetase gene amplification, Bio/Technology 8: 662-667, can be applied. Examples of suitable transfection methods for CHO cells are equally given therein; it is possible to employ e.g. classic calcium phosphate precipitation or more modern lipofection techniques. Transfection rate is routinely defined as the number of positively transfected cells (transient transfection) or clones (stable transfection after selection period) obtained from a pool of cells subjected to transfection. The purported effect of the present object of invention can be seen e.g. by transfecting CHO-K1 cells by lipofection (any commercial reagent and manufacturers protocol) with the plasmids of either Seq. ID No. 3 (pEE 12.4 hCMV-GFP+SV40 early promoter/GS cDNA) or Seq. ID No. 4 (pEE 12.4 mCMV-GFP+SV40 early promoter/GS cDNA). Transfected cells may be grown in any conventional culture medium. The culture medium may be a fetal serum-supplemented or serum-free medium as has been defined above. Preferably, the cell culture medium is a serum-supplemented medium, more preferably a cell culture medium that has been supplemented with at least 1% (v/v) fetal serum, most preferably with at least 5% (v/v) fetal serum such as fetal calf serum or fetal bovine serum. In another preferred embodiment, the transfection method carried out is electroporation.

Experiments

Experiment 1

Transient and Stable Expression of GFP Vector Comprising Hot Spot Sequence in CHO-K1 Cells CHO-K1 cells (ATCC CCL-61) were adapted and cultured in normal cell culture medium GMEM-S (Gibco, UK) with 10% FCS. For GS selection, the medium must be completely free of glutamine as set forth in table 1 below; this necessitates use of dialysed FCS. All culturing was carried out in shake flask at 36.5° C. with orbital shaking at 125 rpm. Lipofectin (Superfectin™, Gibco, UK) was used for transfection and green fluorescence of transfectant pool was measured in a FACS with excitation at 488 nm. For every GS/GFP vector construct, transfection was carried out independently five times, all data being the average from five independently analyzed pools. Starting with transient transfectants 48 h post-transfection, the top scoring 10% highly expressing cells of the viable cell pool in the cell count vs. fluorescence diagram were selected to determine mean fluorescence (FIG. 1). Viable cell population has been preselected by gating in the Forward vs. sideward scatter diagram.

For generating stable transfectants, GS marker was selected 24 hours post-transfection by supplementing the glutamine-free medium with 25 µM MSX (methionine sulphoximine, Crockett et al., ibd.) and continuing cell culture with regular splitting of cultures for 26 days. Note the impact of medium levels of other amino acids on the potency of MSX for selection, see Bebbington et al., U.S. Pat. No. 5,827,739. Fluorescence analysis was then performed again as outlined above (FIG. 2).

Untransfected cells served as negative control. The hot spot vector (pEE 15.1 'hCMV+hot spot') driving expression of GFP under control of the hCMV promoter comprising the first complete intron of CMV is given in Seq. ID No. 1 and essentially is the pEE 15.1 vector shown in FIG. 3 into which the GFP sequence was inserted into the Eco RI restriction site in the polylinker. pEE 12.4 'hCMV' corresponding to Seq. ID No. 3 is identical to pEE 15.1 'hCMV+hot spot' except that it does not comprise the 5.1 kb Bam H1 fragment harboring the IgG 2A sequence. pEE 12.4 served as a vector control. A further vector control pEE 12.4 'hCMV(Kozak-)' was generated by mutating the Kozak sequence of the cloning site coinciding with the translation start site (GCCGCCA CCATGG) to a frameshifted functional Kozak sequence that (ACCATGGTCCATGG) by primer directed mutagenesis (Sambrook et al., Molecular cloning, Cold Spring Harbor 1983), attenuating the original Kozak and translation start site. The vector of Seq. ID No. 1 was further engineered to delete the 400 bp modulator region of hCMV enhancer portion, deleting the enhancer elements upstream of −750 from the transcription start site, giving rise to pEE 15.1 'hCMV (mod−)/GS cDNA'. By exchange of the GScDNA cassette of pEE 15.1 (s. FIG. 3) with the GS minigene of pEE 14.4 'hCMV(mod−)'/GFP, corresponding to Seq. ID No. 2, the vector pEE 15.1 'hCMV(mod−)/GS minigene' was created. Thus all transfected cells harbored a plasmid vector comprising the GFP coding sequence. The GS minigene contains a single, first intron of the GS gene and about 1 kb of 3' flanking DNA under the control of the SV40 late promoter; the 3' part of the genomic GS DNA is believed to cause a higher copynumber of vector DNA and thus of GS in transfected cells (see U.S. Pat. No. 4,770,359, Bebbington et al.). Whereas all hCMV vectors employed in the present study express the GS maker gene from its cDNA sequence, use of the GS minigene was included as a further control in order to exclude potential effects of GS copy number and expression level.

For generation and expression analysis of stably transfected CHO cells, transfections were performed with linearized hot spot vector pEE 15.1 'hCMV+hot spot' vector. Sal I linearized plasmid was cut in the IgG 2A comprising sequence portion, free DNA ends potentially stimulating recombination with genomic regions sharing a certain degree of homology with the flanking DNA portions, testing for potential targeting effects of murine IgG 2A in hamster CHO cells. Pvu I cut in the bacterial lactamase marker gene and therefore could promote but heterologous random recombination. Indeed, the mean fluorescence was higher in the Pvu I linearized transfectants showing both some influence of vector linearization as well as that targeting to immunoglobulin loci in CHO cells may not account for the effect of the present invention. In addition, the effect of enhanced promoter activity was consistently observed in transiently transfected cell populations, nicely correlating with relative strength of individual vector constructs. Clearly, genomic integration is not involved at this early stage of transfection.

FIG. 3 shows vector pEE 15.1 of approximately 12 830 bp. A detailed description of the GS marker and the hCMV-p/ intron expression cassette can be found in U.S. Pat. Nos. 5,827,739 and 5,591,639. pEE 15.1 is a possible embodiment of an expression vector according to the present invention, except that the DNA sequence coding for the recombinant product protein has not yet been inserted in the polylinker site. The complete 13535 bp sequence of the pEE15.1 construct harboring GFP is given in Seq. ID No. 1: Therein, the GFP coding sequence was inserted in-frame in the Eco R I restriction site centered at base position 12 814; the introduction of the unique restriction site harboring the ATG start codon and optimizing the Kozak sequence environment of the start codon is described in detail in U.S. Pat. No. 5,591,639. Thus, the expression of GFP protein is under control of the hCMV-major immediate early gene promoter (HCMV-MIE or hCMV for short) immediately followed by the first intron of hCMV-MIE gene followed by the Nco I site (s. U.S. Pat. No. 5,591,639). Polyadenlyation is ensured by the SV40 poly A site further downstream of the polylinker insertion site. pEE 15.1 further harbors a cDNA sequence coding for glutamine synthetase (GS) from hamster that is under control of the SV40 early promoter and is followed by an SV40 intron+poly A sequence. The IgG 2A gene locus or 'hot spot' sequence (hatched boxes CH1, Hi, $CH_2$, $CH_3$, M1, M2 standing for Heavy chain constant region, hinge, membrane anchor) is the 5.1 kb BamHI fragment of the murine IgG 2 A locus already described in WO 9517516 and the references cited therein. Unique restriction sites Pvu I and Sal I are shown.

Experiment 2

Electroporation of CHO Cells with mCMV p12.4-GFP Construct (Seq. ID No. 4)

Attached CHO-K1 cells (ATCC CCL-61) were cultured in Iscoves' DMEM medium essentially as described in EP-481 791 comprising 2 mM Glutamine which was further supplemented with 10% FCS. Optionally, the G-MEM medium stated in table 1 and further comprising 2 mM Glutamine could be used prior to GS marker selection as in experiment 1. The cells were detached, pelleted and resuspended twice in serum-free medium, finally at a density of $5.3 \times 10^6$ cells/ml. Per 750 µl electroporation batch, a total of $4 \times 10^6$ cells was electroporated. Electroporation was carried out as described in Methods in Molecular Biology, ed. J A Nickoloff ed, Humana Press 1995, Vol. 48/Chap. 8: Animal cell electroporation and electrofusion protocols. p12.4 mCMV-GFP vector DNA (sequence ID No. 4) was linearized. 50 µl (20 µg) DNA were added to 750 µl cells in electroporation cuvette and electroporate—300 Volts/750 µFd—expecting an electroporation time of around 12-14 msec. Following electroporation 800 µl volume of cells was transferred into 25 ml of modified Glasgow-MEM (GMEM, Gibco) culture medium for GS selection (comprising 10% fetal serum but no glutamine, for details see table 1) in a T75 flask. Divide into 2× T75 flasks by moving 12.9 mls into a second flask and incubate overnight at 37° C. in 10% $CO_2$ On the next day 37.5 ml of GS-selection GMEM culture medium supplemented with 10% FBS+33.3 µM MSX (methionine sulphoximine) were added. Thus MSX was finally ~25 µM. Transfectants were counted after further incubation for 26 days by colony count per flask. Upon microscopic inspection in a standard inverted microscope for inspection of culture flasks, positive colonies brightly lit up in light green and could be easily counted.

The mCMV construct of Seq. ID No. 4 yielded up to 20 times more foci than did cells that were transfected in parallel with the hCMV construct of Seq. ID No. 3. The vector constructs only differed in the CMV promoter elements driving GFP expression, the remaining vector parts of the vectors were identical (including GS-marker; cDNA GS-marker cassette of p12.4). If cells were diluted out into 96 well plates immediately following transfection, many more colonies come up from mCMV transfected cells (>400 colonies) than from hCMV transfected cells (about 45 colonies).

TABLE 1

Medium for GS selection

A. Stock Solutions

1. Double distilled water autoclaved in 400 ml aliquots
2. 10 × Glasgow MEM (GMEM) without glutamine (GIBCO: 042-2541 in UK). Store at 4° C.
3. 7.5% sodium bicarbonate (GIBCO: 043-05080 in UK; 670-5080 in US). Store at 4° C.
4. 100 × non-essential amino acids (NEAA) (GIBCO: 043-01140 in UK; 320-1140 in US). Store at 4° C.
5. 100 × Glutamate + Asparagine (G + A): add 600 mg glutamic acid and 600 mg asparagines (Sigma). Make up to 100 ml in distilled water and sterilize by passing through a sterile 2 μm filter (Nalgene). Store at 4° C.
6. 100 mM sodium pyruvate (GIBCO: 043-01360 in UK; 320-1360 in US)
7. 50 × nucleosides: 35 mg adenosine
35 mg guanosine
35 mg cytidine
35 mg uridine
12 mg thymidine
(each from Sigma). Make up to 100 ml with water, filter sterilise and store at −20° C. in 10 ml aliquots.
8. Dialysed FCS (GIBCO: 014-06300). Heat inactivate at 56° C. for 30 min and store at −20° C. It is essential to use dialysed FCS when using GS selection.
9. Penicilin-streptomycin at 5000 units/ml (P/S: GIBCO: 043-05070 in UK; 600-5070 in US).
10. 100 mM L.MSX (Sigma): prepare 18 mg/ml solution in PBS. Filter sterilise and store at −20° C.

B. Medium Preparation

Add the following in the order given using aseptic technique to make GMEM-S medium

| | | |
|---|---|---|
| 1. Water | 400 | ml |
| 2. 10 × GMEM | 50 | ml |
| 3. Sodium bicarbonate | 18.1 | ml |
| 4. NEAA | 5 | ml |
| 5. G + A | 5 | ml |
| 6. Sodium pyruvate | 5 | ml |
| 7. Nucleosides | 10 | ml |
| 8. Dialysed FCS | 50 | ml |
| 9. Penicillin-streptomycin | 5 | ml |

GMEM-S contains the non-essential amino acids, alanine, aspartate, glycine, proline and serine (100 μM), glutamate and asparagines (500 μM), and adenosine, guanosine, cytidine and uridine (30 μM), and thymidine (10 μM).

The invention claimed is:

1. The method for enhancing the transfection rate of a mammalian expression vector in CHO cells by transfecting the cells with an expression vector that comprises a transcription unit for a product gene which transcription unit is under control of the mCMV promoter, said vector further comprising a portion from the murine IgG 2A gene locus which portion is enhancing the activity of the mCMV promoter.

2. The method according to claim 1 wherein the expression vector further comprises a second transcription unit comprising a glutamine synthetase (GS) marker gene.

3. The method according to claim 1, characterized in that the mCMV promoter comprises the natural transcription start site (+0) and extends upstream to position −500.

4. The method according to claim 3, characterized in that the mCMV promoter extends to the natural Xho I restriction site.

5. The method according to claim 1, characterized in that the mCMV promoter lacks the first, natural intron of the mCMV promoter.

* * * * *